United States Patent
Kawano et al.

(10) Patent No.: US 11,118,977 B2
(45) Date of Patent: Sep. 14, 2021

(54) TERAHERTZ WAVE DETECTION DEVICE AND TERAHERTZ WAVE DETECTION SYSTEM

(71) Applicant: Tokyo Institute of Technology, Tokyo (JP)

(72) Inventors: Yukio Kawano, Tokyo (JP); Daichi Suzuki, Tokyo (JP)

(73) Assignee: Tokyo Institute of Technology, Tokyo (JP)

( * ) Notice: Subject to any disclaimer, the term of this patent is extended or adjusted under 35 U.S.C. 154(b) by 38 days.

(21) Appl. No.: 16/608,684

(22) PCT Filed: May 9, 2018

(86) PCT No.: PCT/JP2018/017921
§ 371 (c)(1),
(2) Date: Oct. 25, 2019

(87) PCT Pub. No.: WO2018/207815
PCT Pub. Date: Nov. 15, 2018

(65) Prior Publication Data
US 2020/0141806 A1    May 7, 2020

(30) Foreign Application Priority Data
May 9, 2017   (JP) .............................. JP2017-093256

(51) Int. Cl.
*G01J 5/02*   (2006.01)
*G01N 21/3581*   (2014.01)

(52) U.S. Cl.
CPC .......... *G01J 5/023* (2013.01); *G01N 21/3581* (2013.01)

(58) Field of Classification Search
CPC ........ G01J 5/023; G01J 5/0225; G01J 5/0853; G01J 3/42; G01N 21/3581; G01N 2021/95676
See application file for complete search history.

(56) References Cited

U.S. PATENT DOCUMENTS 10,392,520 B2 * 8/2019 Zhou ...................... C09D 11/32
2002/0049389 A1   4/2002 Abreu
(Continued)

FOREIGN PATENT DOCUMENTS

| JP | 2005-502389 A | 1/2005 |
| JP | 2010-060284 A | 3/2010 |

(Continued)

OTHER PUBLICATIONS

Erikson, Kristopher J., et al. "Figure of Merit for Carbon Nanotube Photothermoelectric Detectors." *ACS Nano*, vol. 9, No. 12, pp. 11618-11627 (American Chemical Society, 2015).
He, Xiaowei, et al. "Carbon Nanotube Terahertz Detector." *Nano Letters* 14, pp. 3953-3958 (American Chemical Society, 2014).
(Continued)

*Primary Examiner* — David P Porta
*Assistant Examiner* — Meenakshi S Sahu
(74) *Attorney, Agent, or Firm* — The Marbury Law Group, PLLC

(57) ABSTRACT

Provided are a terahertz wave detection device and a terahertz wave detection system to execute checking at high speed with high sensitivity and accuracy and to execute omnidirectional inspection without requiring a large checking system. A flexible array sensor (30) includes: a terahertz wave detection element (10) having a flexible single-walled carbon nanotube film (11), and a first electrode (12) and a second electrode (13) disposed to face each other on a two-dimensional plane of the single-walled carbon nanotube film (11); and a flexible substrate (20) having flexibility to (Continued)

support the terahertz wave detection element (10) so as to be freely curved. The flexible substrate (20) is preferably formed in a curved or cylindrical shape, so that the terahertz wave detection elements (10) are arrayed on the flexible substrate 20 formed in a curved or cylindrical shape.

18 Claims, 22 Drawing Sheets

(56) References Cited

U.S. PATENT DOCUMENTS

| | | | |
|---|---|---|---|
| 2010/0051812 A1* | 3/2010 | Kawano | H01L 31/112 250/338.2 |
| 2013/0225988 A1 | 8/2013 | Mahfouz | |
| 2013/0277558 A1 | 10/2013 | Yamamura | |
| 2015/0051496 A1 | 2/2015 | Ouchi | |
| 2017/0279052 A1* | 9/2017 | Falk | H01L 51/0025 |

FOREIGN PATENT DOCUMENTS

| | | |
|---|---|---|
| JP | 2013-190350 A | 9/2013 |
| JP | 2013-221907 A | 10/2013 |
| WO | WO 2016/060225 A1 | 4/2016 |
| WO | WO 2017/188438 A1 | 11/2017 |

OTHER PUBLICATIONS

Kawano, Yukio. "Terahertz Response of Carbon Nanotubes and Graphene." *Journal of the Physical Society of Japan*, vol. 84, pp. 121010.1-121010.9 (2015).

Kawano, Yukio. "Terahertz detectors, spectrometers, and images based on low- dimensional electron systems." *Journal of the Physical Society of Japan of "Oyobuturi"*, vol. 84, pp. 643-647 (2015). [English abstract].

Suzuki, D., et al. "A flexible terahertz scanner for multi-view terahertz imaging." The 78th JSAP Autumn Meeting, Aug. 25, 2017, Sp-A405-10. [English abstract].

Suzuki, D. et al. "A flexible and wearable terahertz scanner." *Nature Photonics*, vol. 10, pp. 809-813 (Nov. 14, 2016), DOI: http://dx.doi.org/10.1038/NPHOTON.2016.209.

* cited by examiner

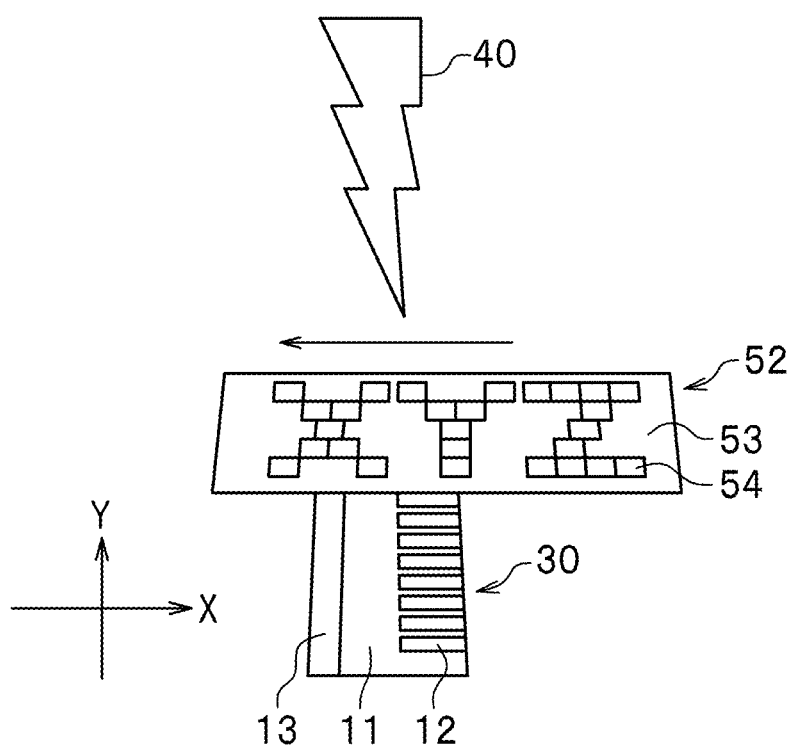

Scan along X-axis

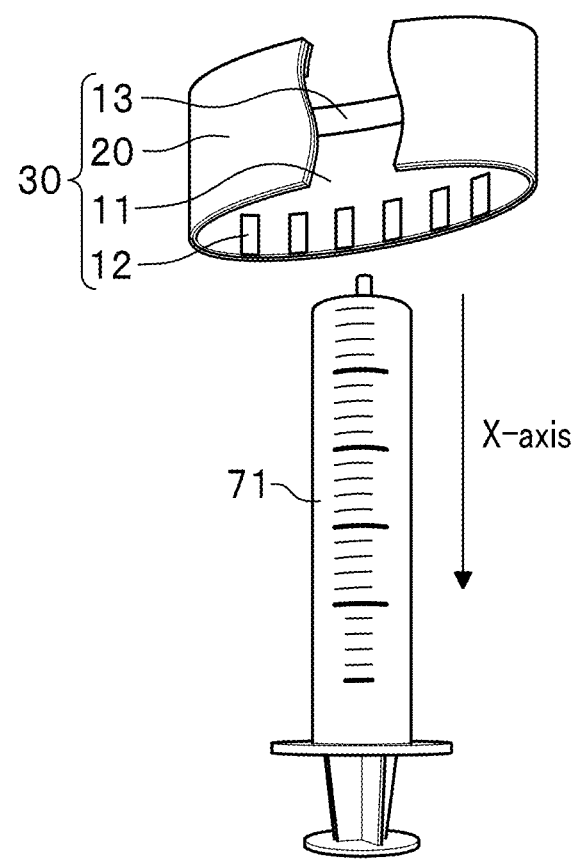

US 11,118,977 B2

TERAHERTZ WAVE DETECTION DEVICE AND TERAHERTZ WAVE DETECTION SYSTEM

RELATED APPLICATIONS

This application is a national phase entry of international patent application PCT/JP2018/017921 filed May 9, 2018, which claims benefit of priority to Japanese Application Serial No. 2017-093256, filed May 9, 2017, the entire disclosures of which are incorporated herein by reference in their entireties.

TECHNICAL FIELD

The present invention relates to a terahertz wave detection device and a terahertz wave detection system.

BACKGROUND ART

A terahertz (THz) wave is an electromagnetic wave in a frequency range of 0.1 to 30 THz (1 THz equals to $10^{12}$ Hz), that is, an electromagnetic wave having a wavelength ranging from that of a submillimeter wave, nearly 0.01 mm to 3 mm, to that of a far infrared wave. A THz wave is at an ultimate level of high-frequency waves for electronic control by electronics as well as at an ultimate level of low-energy waves for light control by optics or photonics, and therefore has been unexploited. This is the reason that basic elements such as a wave source and a detector are unexploited for THz waves, as compared with those for light/waves in other frequency bands. In addition, the wavelength of the THz wave is two or three orders of magnitude longer than that of visible light, to have low spatial resolution of imaging.

Patent Document 1 discloses a terahertz wave detecting apparatus including: a semiconductor chip formed to have two-dimensional electron gas at a predetermined distance from a surface thereof; a carbon nanotube closely attached to the surface of the semiconductor chip; a conductive source electrode; a drain electrode; and a gate electrode. The carbon nanotube extends along the surface of the semiconductor chip, and both ends thereof are respectively connected to the source electrode and the drain electrode, and the gate electrode is positioned at a predetermined distance from a side surface of the carbon nanotube. The terahertz wave detecting apparatus further includes: an SD current detection circuit that applies a predetermined voltage between the source electrode and the drain electrode to detect an SD current flowing therebetween; a gate voltage application circuit that applies a variable gate voltage between the source electrode and the gate electrode; and a magnetic field generator that applies a variable magnetic field to the semiconductor chip.

Other detectors to detect frequencies of terahertz waves are disclosed in Non-patent Documents 1 to 4, for example. Detectors to select a frequency are disclosed in Non-patent Documents 3 and 4. Conventional THz wave detector excites one conduction electron as one photon is absorbed, to inevitably have limitation in detection sensitivity. In contrast, Non-patent Document 4 discloses a new technique of detecting, dispersing, and imaging THz waves using features of low-dimensional electron systems such as a carbon nanotube (CNT) array, graphene, and two-dimensional electron gas (2DEG) at a semiconductor heterointerface. Non-patent Document 4 discloses a new mechanism to produce a hybrid structure, having a carbon nanotube (CNT) quantum dot coupled with 2DEG in a semiconductor, to detect a carrier excited in a two-dimensional electron gas by a high-sensitivity charge sensor using a CNT.

PRIOR ART DOCUMENTS

Patent Documents

Patent Document 1: Japanese Patent Application Publication No. 2010-060284

Non-Patent Documents

Non-patent Document 1: Xiaowei He, Naoki Fujimura, J. Meagan Lloyd, Kristopher J. Erickson, A. Alec Talin, Qi, Zhang, Weilu Gao, Qijia Jiang, Yukio Kawano, Robert H. Hauge, Francois Leonard and Junichiro Kono, "Carbon Nanotube Terahertz Detector," Nano Letters 14, pp. 3953-3958 (2014)

Non-patent Document 2: Kristopher Erickson, Xiaowei He, A. Alec Talin, Bernice Mills, Robert H. Hauge, Takashi Iguchi, Naoki Fujimura, Yukio Kawano, Junichiro Kono, Francois Leonard, "Figure of Merit for Carbon Nanotube Photothermoelectric Detectors," ACS Nano 9, pp. 11618-11627 (2015)

Non-patent Document 3: Yukio Kawano, "Terahertz Response of Carbon Nanotubes and Graphene," Journal of the Physical Society of Japan Vol. 84, pp. 121010.1-121010.9 (2015)

Non-patent Document 4: Yukio Kawano, "Terahertz Detectors, Spectrometers, and Imagers based on Low-dimensional Electron Systems," Journal of the Physical Society of Japan Vol. 84, pp. 643-647

SUMMARY OF THE INVENTION

Problems to be Solved

Non-patent Documents 1 to 4 are silent about optimum conditions of materials and electrodes when carbon nanotubes are used as a terahertz detector or an array sensor. Many of the conventional techniques belong to a scanning type to take a long time for imaging check. In addition, the conventional detectors cannot be curved, to have a problem that single detector is not enough for imaging from the entire field of vision.

The present invention has been made in view of such circumstances and is intended to provide a terahertz wave detection device and a terahertz wave detection system to execute checking at high speed with high sensitivity and high accuracy and to execute omnidirectional inspection without requiring a large checking system.

Solution to Resolve Problems

In order to resolve the problems described above, a terahertz wave detection device of the present invention includes a terahertz wave detection element that has a flexible carbon nanotube film, and a first electrode and a second electrode which are disposed to face each other on a two-dimensional plane of the carbon nanotube film.

A terahertz wave detection system of the present invention includes the terahertz wave detection device as claimed in any one of claims 1 to 7 as appended, and a data collection device to collect physical data detected by the terahertz wave detection device.

Advantageous Effects of the Invention

The present invention provides a terahertz wave detection device to execute checking at high speed with high sensitivity and high accuracy and to execute omnidirectional inspection without requiring a large checking system.

BRIEF DESCRIPTION OF DRAWINGS

FIG. 10 illustrates an overall checking system using the terahertz wave detection device according to the present embodiment;

FIG. 17 illustrates omnidirectional flexible imaging of a curved sample (syringe) by the terahertz wave detection device according to the present embodiment as a checking system using a flexible array sensor;

EMBODIMENTS OF THE INVENTION

Figure 1:
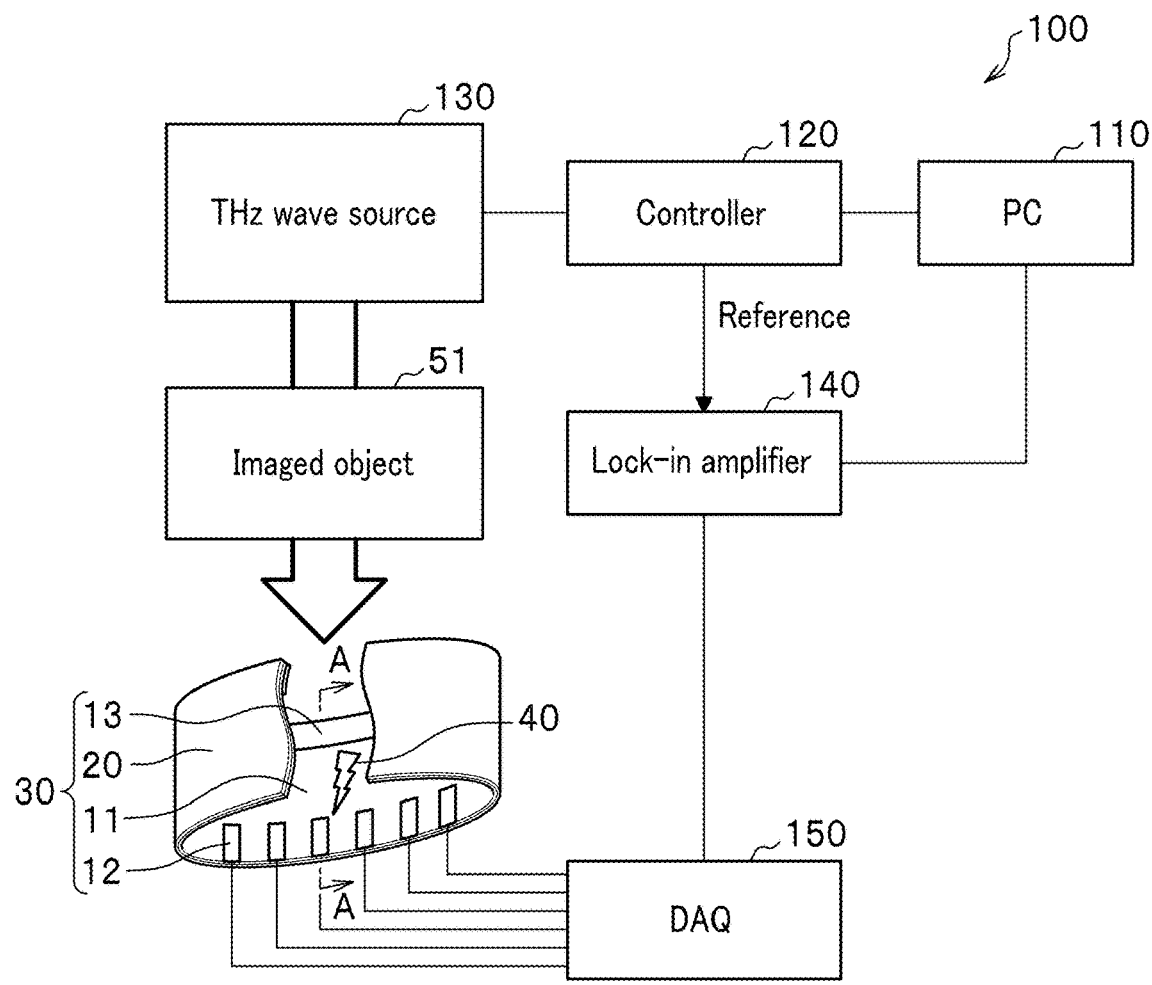
FIG. 1 is a block diagram of an overall terahertz wave detection system according to one embodiment of the present invention.

Hereinafter, embodiments of the present invention will be described in detail with reference to the drawings. FIG. 1 is a block diagram of an overall terahertz wave detection system according to an embodiment of the present invention. As shown in FIG. 1, a terahertz wave detection system 100 includes a flexible array sensor 30 (terahertz wave detection device), a PC (personal computer) 110 to control the entire device, a controller 120, a THz wave source 130, a lock-in amplifier 140, and a DAQ (Data AcQuisition) 150 (or data acquisition device).

The THz wave source 130 is configured to include a photoconductive antenna (PCA) and a generating element, inclusive of a resonant tunneling diode (RTD), for example. A terahertz wave generated by the terahertz wave generating element is efficiently extracted by a silicon lens and emitted as a terahertz wave beam by a collimator lens. The THz wave source 130 may be configured, as another example, to includes a light source to emit femtosecond pulse laser light, as excitation light, and an oscillation unit to receive the femtosecond pulse laser light emitted from the light source and generate a THz wave, for example, and to irradiate a checked object 51 with the THz wave.

The flexible array sensor 30 detects the terahertz waves outputted from the THz wave source 130 and then transmitted through the checked object 51 (details will be described below).

The controller 120 controls the THz wave source 130. The controller 120 outputs a reference signal to the lock-in amplifier 140.

The lock-in amplifier 140 includes a multiplier and a low pass filter, receives the reference signal from the controller 120, and detects a frequency component equal to the reference signal. The lock-in amplifier 140 allows only the frequency component, equal to the reference signal, of various signals included in the checked signal to flow as a direct current and pass through the low pass filter. Other frequency components are converted to alternating current signals and thus removed by the low pass filter. The lock-in amplifier 140 reduces noise and increases S/N (signal-to-noise ratio). Note that the lock-in amplifier 140 may be dispensed with, if sufficient S/N is obtained.

The DAQ 150 collects and checks data representing electrical and physical phenomena of voltage and current detected by the flexible array sensor 30. Here, a switch may be provided instead of, or in combination with, the DAQ 150. The switch reads out multi-channel signals from the flexible array sensor 30 while shifting the read-out timing for respective terahertz wave detection elements 10 of the flexible array sensor 30. Additionally, when the flexible array sensor 30 is configured to be wearable, a wireless device is incorporated in the flexible array sensor 30 instead of, or in combination with, the DAQ 150, to transmit data wirelessly. The wireless device may utilize near-field radio communication (NFC) or Bluetooth (registered trademark) protocol, for example. Note that the DAQ 150, the switch, the wireless device and the like may be integrated on a single-walled carbon nanotube film 11 (to be described below).

The PC 110 controls the controller 120 to regulate the wavelength of THz wave outputted from the THz wave source 130. The PC 110 also controls the lock-in amplifier 140 to reduce noise so that a detection signal to be obtained by the flexible array sensor 30 is surely obtained.

Flexible Array Sensor 30

The flexible array sensor 30 is an 8-element array sensor (or an 8-element array detector) in which eight terahertz wave detection elements 10 (also see FIG. 2) are aligned. The 8-element array sensor (flexible array sensor 30) has a structure of eight terahertz wave detection elements 10 having a width of 1 mm being arranged at intervals of 0.5 mm. When the terahertz wave detection device 10 is viewed from above, the vertical length is 1 mm, and a distance between electrodes of the terahertz wave detection devices 10 is 1.5 mm. The eight-element array sensor 30 is moved in the X-Y direction to detect THz waves in a two-dimensional area of 8×8. The flexible array sensor 30 includes the terahertz wave detection element 10 and a flexible substrate 20 having a plurality of terahertz wave detection elements 10 fixed thereon in array.

<Flexible Substrate>

The flexible substrate 20 is a flexible support substrate of a flexible single-walled carbon nanotube film 11 (to be described below). The flexible substrate 20 is made of a polymer material, for example, and may be transparent. The flexible substrate 20 may be a substrate made of any material, as long as it satisfies conditions required for a support substrate such as no noise generation, low thermal conductivity, insulation, weather resistance, and predetermined strength in addition to flexibility and plasticity.

The present embodiment is configured so that the flexible single-walled carbon nanotube film 11 is supported by the flexible substrate 20. The present invention is not limited to this configuration and the flexible substrate 20 may not be used as a support substrate, as long as the carbon nanotube film (single-walled carbon nanotube film 11) has a certain thickness, which configuration is also possible in principle. However, the carbon nanotube film itself is freely bent in reality without support by any supporting means, and then the flexible substrate 20 is preferably used for support.

Terahertz Wave Detection Element 10

Figure 2:
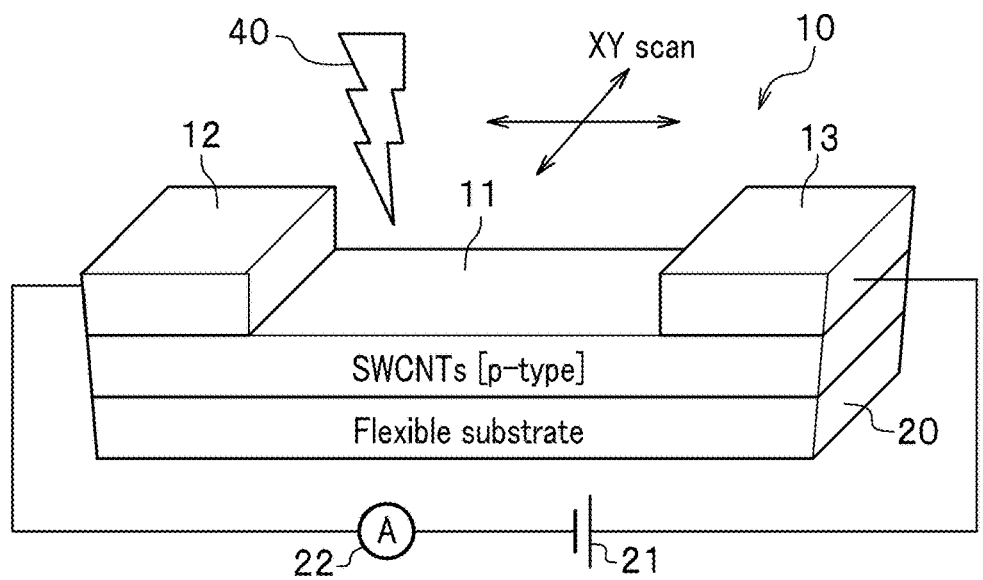
FIG. 2 is a perspective view of a terahertz wave detection element of the terahertz wave detection device according to the present embodiment.

FIG. 2 is a perspective view of the terahertz wave detection element 10. FIG. 2 is a cross-sectional view taken along an arrowed line A-A in FIG. 1. The terahertz wave detection device 10 of the present embodiment provides optimum conditions of the material and electrodes 12, 13. As shown in FIG. 2, the terahertz wave detection element 10 (terahertz wave detection device) includes a flexible single-walled carbon nanotube film (SWCNT film) 11 (low-dimensional electron-based material) integrated on the flexible substrate 20 at high density, a first electrode 12 at one end of the single-walled carbon nanotube film 11, and a second electrode 13 at the other end thereof. The single-walled carbon nanotube film 11 between the first electrode 12 and the second electrode 13 is irradiated with THz waves 40 in the infrared region.

<Single-Walled Carbon Nanotube Film>

A carbon nanotube has high electrical conductivity, high mechanical strength, and flexibility. A carbon nanotube absorbs electromagnetic waves in a very wide frequency band ranging from frequencies close to DC to ultraviolet. In particular, it absorbs light in a very wide frequency band ranging from sub-terahertz waves to ultraviolet. The present inventors previously revealed that carbon nanotubes can be used as a terahertz detector. However, the optimum conditions of the material and electrode constituting a detector were not identified. In the present embodiment, optimum conditions of materials and electrodes are provided. First, a carbon nanotube as a material has the following characteristics. In the single-walled carbon nanotube film 11, the single-walled carbon nanotubes are arrayed in high density longitudinally from a far end of the first electrodes 12 to a far end of the second electrode 13. In order to further enhance the detection sensitivity, one having higher orientation is desired. The single-walled carbon nanotube film 11 is a p-type as an example. Alternatively, the single-walled carbon nanotube film 11 may be an n-type or may be a combination of a p-type and an n-type. The single-walled carbon nanotube film 11 is a carbon nanotube thin film having a film thickness of 50 micrometer, for example.

The single-walled carbon nanotube film 11 is preferably a single-walled carbon nanotube. The single-walled carbon nanotube film 11 preferably contains 50% by weight or more of the single-walled carbon nanotubes, and more preferably 80% by weight or more. More preferably, a single-walled carbon nanotube may be used that has a ratio of the value of standard deviation multiplied by 3 to the mean diameter (3×standard deviation/mean diameter) being greater than 0.20 but less than 0.60, and has t-plots obtained from an adsorption isotherm curve being in a convex upward shape. The single-walled carbon nanotube film 11 may be made from one of, or in combination of, single-walled carbon nanotubes (SWCNTs), double-walled carbon nanotubes (DWCNTs), and multi-walled carbon nanotubes (MWCNTs).

<First Electrode and Second Electrode>

The first electrode 12 and the second electrode 13 are made of metal. The first electrode 12 and the second electrode 13 are made of Au, for example. Other electrode materials include Al, Mo, Ni, and Ti. However, those also used include: precious metals such as Cu, Ag, and Pt other than Au; Al group elements such as Ga and In other than Al; chromium group elements such as Cr and W other than Mo; iron group elements such as Fe and Co other than Ni; tin-group elements such as Zr, Sn, Hf, Pb, and Th other than Ti; magnesium-group elements such as Be, Mg, and Zn; and alloys of these metals. When the single-walled carbon nanotube film 11 near the first electrode 12 is irradiated with terahertz waves to generate an electromotive force, the first electrode 12 works as a source electrode and the second electrode 13 works as a drain electrode. A battery 21 and an ammeter 22 are connected between the first electrode 12 and the second electrode 13. Note that the distance, in the longitudinal direction of the single-walled carbon nanotube film, of the first electrode 12 and the second electrode 13 is set to 1.5 mm, and the distance between the far ends of the first electrode 12 and the second electrode 13 is set to 20 mm, as an example.

Figure 3:
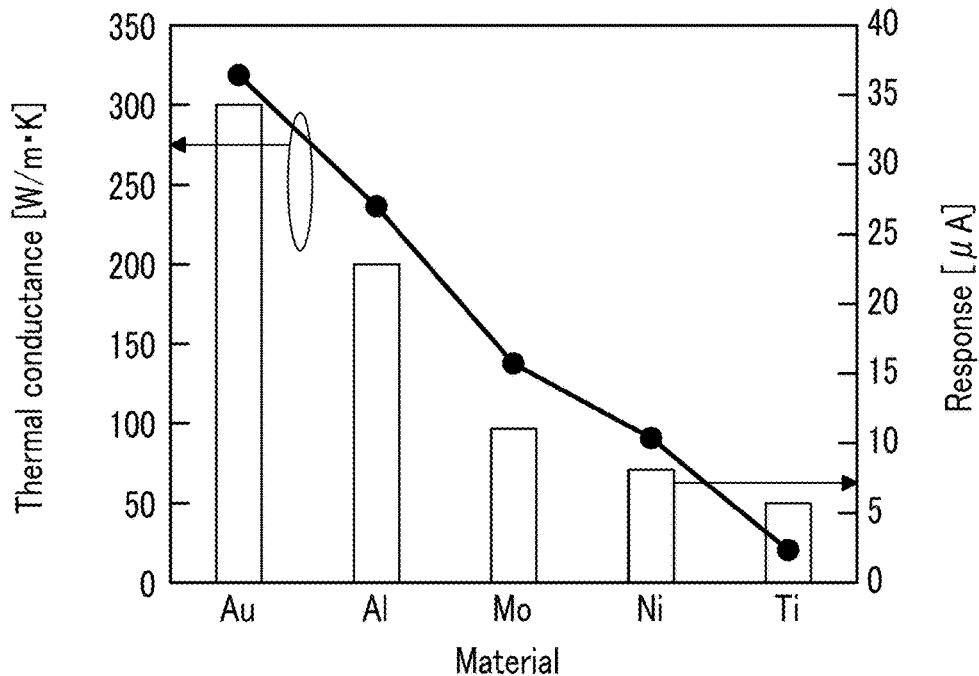
FIG. 3 is a chart showing the thermal conductivity and sensitivity of a material (Au, Al, Mo, Ni, Ti) of an electrode in the terahertz wave detection device according to the present embodiment.

FIG. 3 is a chart showing the thermal conductivity [W/(m*K)] and the response signal (Response [μA], with right vertical axis) of the material (Au, Al, Mo, Ni, Ti) of the electrode. The response signal (Response [μA]) is indicated by the response current. In FIG. 3, the thermal conductivity of the material of the electrode is shown in the form of the line graph (with left vertical axis) and the response signal is shown in the form of the bar graph (with right vertical axis). As shown in FIG. 3, the response currents (Response [μA]) of the respective electrodes vary in descending order of Au, Al, Mo, Ni, Ti. The response current of Au is the largest among the materials of the electrodes shown in FIG. 3, followed by that of Al. The sensitivity of Mo is approximately halved from that of Al, followed by those of Ni and Ti. The sensitivity is related to the thermal conductivity. That is, the higher the thermal conductivity is, the higher the sensitivity is, as shown in FIG. 3. When the thermal conductivity of the electrode is increased, the detection sensitivity is improved.

Figure 4:
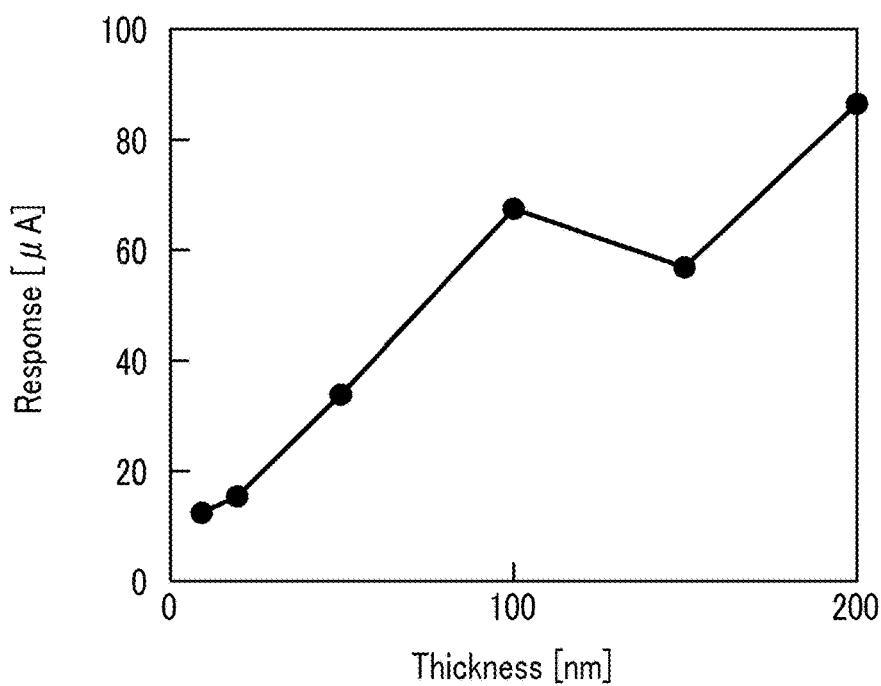
FIG. 4 is a chart showing the relationship of the response sensitivity to the thickness of the electrode when a checked object is irradiated with THz waves in frequency of 29 THz from the terahertz wave detection device according to the present embodiment.

FIG. 4 is a chart showing the relationship of the response signal (response current) (Response [μA]) to the thickness (Thickness [nm]) of the electrode when a checked object is irradiated with THz waves in frequency of 29 THz. The thicker the electrode (Au, for example) is, the higher the sensitivity is. In order to increase the response signal, the thickness of the electrode needs to be increased.

From the above description, a group of (Au, Al) and a group of (Mo, Ni, Ti) should be combined among the materials for the electrode shown in FIG. 3, from the viewpoint of using metals having asymmetric thermal conductivities. Here, from the viewpoint of improving detection sensitivity, Au having a large thermal conductivity should be selected. Therefore, when Au is selected for one electrode, the other electrode may be selected from the group of (Mo, Ni, Ti). In this case, Ti may preferably be used for the other electrode, in order to increase the difference between the thermal conductivities of the electrodes.

Figure 5:
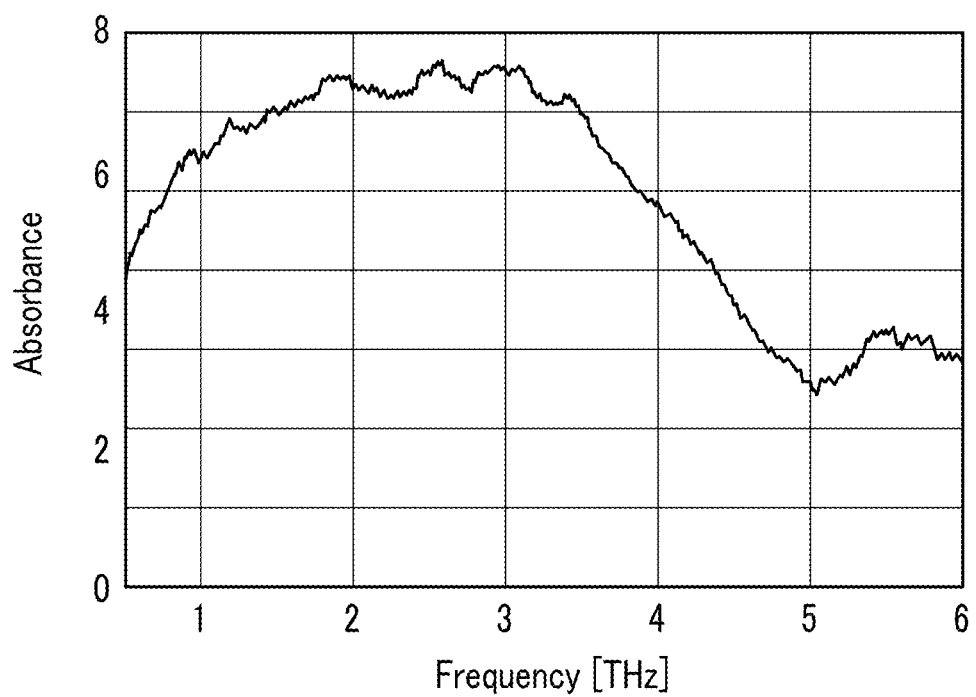
FIG. 5 is a chart showing an electromagnetic wave absorption spectrum of the terahertz wave detection device according to the present embodiment.

FIG. 5 is a chart showing an electromagnetic wave absorption spectrum of the terahertz wave detection element 10 (single-walled carbon nanotube film 11). The horizontal axis indicates the frequency (Frequency [THz]) and the vertical axis indicates the electromagnetic wave absorption (Absorbance). As shown in FIG. 5, the terahertz wave detection element 10 absorbs electromagnetic waves in a wide frequency band of 0.5 THz to 6 THz. As described above, the single-walled carbon nanotube film 11 is integrated in high density, longitudinally from the far end of the first electrode 12 to the far end of the second electrode 13. Therefore, the single-walled carbon nanotube film 11 absorbs electromagnetic waves in a wide frequency band.

Figure 6A:
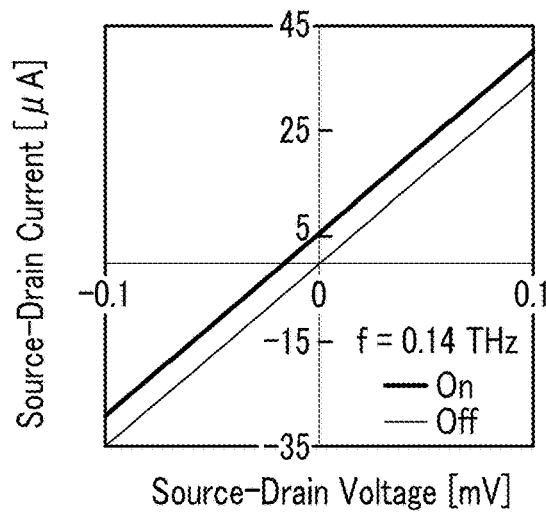
FIG. 6A is a chart showing the I-V characteristics of the terahertz wave detection device of the present embodiment being shifted, when the checked object is irradiated with THz waves in frequency of 0.14 THz.
Figure 6B:
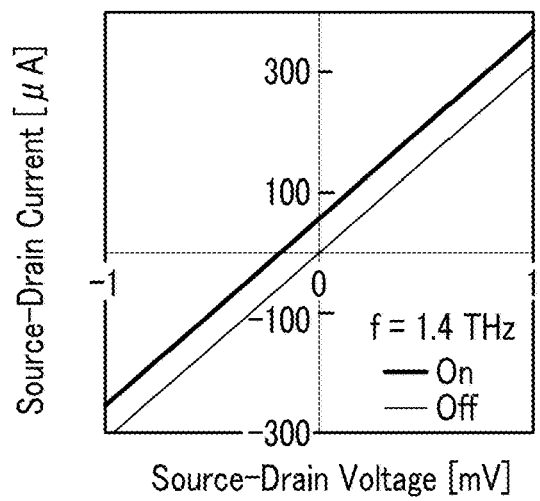
FIG. 6B is a chart showing the I-V characteristics of the terahertz wave detection device of the present embodiment being shifted, when the checked object is irradiated with THz waves in frequency of 14 THz.
Figure 6C:
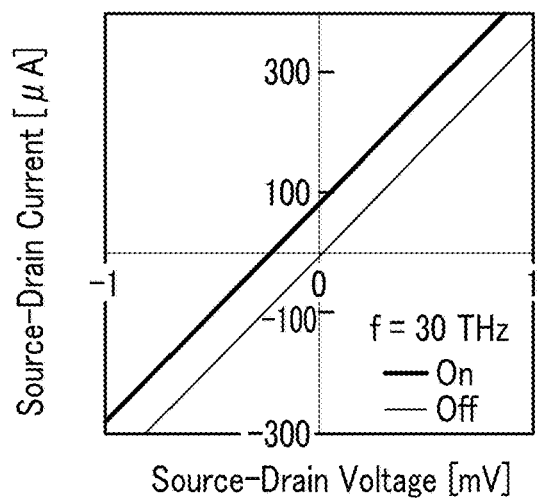
FIG. 6C is a chart showing the I-V characteristics of the terahertz wave detection device of the present embodiment being shifted, when the checked object is irradiated with THz waves in frequency of 30 THz.

FIGS. 6A to 6C are charts showing the I-V characteristics of the terahertz wave detection device 10 and the results of the response to the THz waves (under room temperature). The horizontal axis indicates the source-drain voltage [mV] and the vertical axis indicates the source-drain current [μA]. The thin solid line in the I-V characteristics in FIGS. 6A to 6C indicates a case having no irradiation with THz waves (Off), and the thick solid line indicates a case having irradiation with THz waves (On). As shown in FIG. 6A, the I-V characteristics were linear and a shift of the I-V characteristics was observed, when the checked object was irradiated with THz waves in frequency of 0.14 THz. As shown in FIG. 6B, the I-V characteristics were linear and a shift of the I-V characteristics was observed, when the checked object was irradiated with THz waves in frequency of 14 THz. As shown in FIG. 6C, the I-V characteristics were linear and a shift of the I-V characteristics was observed, when the checked object was irradiated with THz waves in frequency of 30 THz. There is no change in the slope of the I-V characteristics (electrical resistance remains unchanged) in any of the cases having irradiation with THz waves, and then there is no association with simple bolometric effects (the effects of temperature being increased due to absorption of THz waves). The dependency on the thermal conductivity of the substrate (flexible substrate 20), on which the single-walled carbon nanotube film 11 is mounted, has been checked to find that the smaller the thermal conductivity is, the larger the THz response is. This fact means that the THz response increases as the heat is accumulated in the CNT, without the heat generated as a result of irradiation with THz waves escaping through the substrate, to make the photothermal effect expected as a THz detection mechanism.

Figure 7:
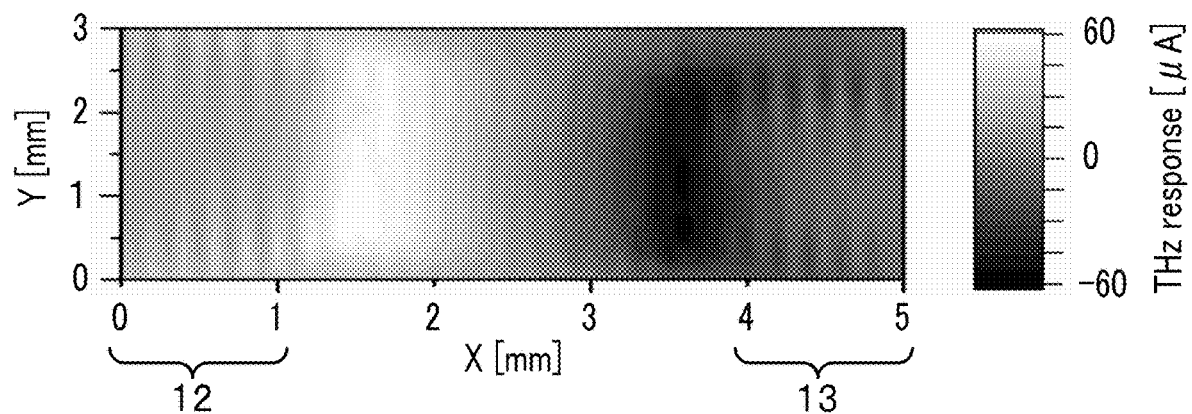
FIG. 7 is a chart showing response signals (response currents) on the X-Y plane of a single-walled carbon nanotube film of the terahertz wave detection device according to the present embodiment.

FIG. 7 is a chart showing response signals (response currents) (Response [μA]) on the X-Y plane of the single-walled carbon nanotube film 11. A portion having high contrast in FIG. 7 has high response. The positive/negative and sensitivity of the response signal are detected such that the left side in FIG. 7 is indicated by positive signals (white), as the positive side of the response signal (Response [μA]), while the right side in FIG. 7 is indicated by negative signals (black), as the negative side of the response signal (Response [μA]). Two portions having high sensitivity, on the X-Y plane of the single-walled carbon nanotube film 11, are located in the vicinity of the respective electrodes.

In order to serve as a camera, a detection unit needs to be made as small as possible. However, if it is made smaller, the two electrodes come closer so that a positive signal and a negative signal are mixed to be canceled. In order to avoid this phenomenon, the detection unit has an asymmetric electrode structure. This allows for reading out a signal from only one electrode, to avoid the problem of signal cancellation due to reduction in size. Then, metals having asymmetric thermal conductivities are used for the respective electrodes to implement an asymmetric electrode structure. Au having high thermal conductivity is used for one electrode and Ti having low thermal conductivity is used for the other electrode, for example, to separate the portions having high sensitivity from either one of the electrodes. This allows for reading out response from only one electrode to obtain an accurate image.

Figure 8:
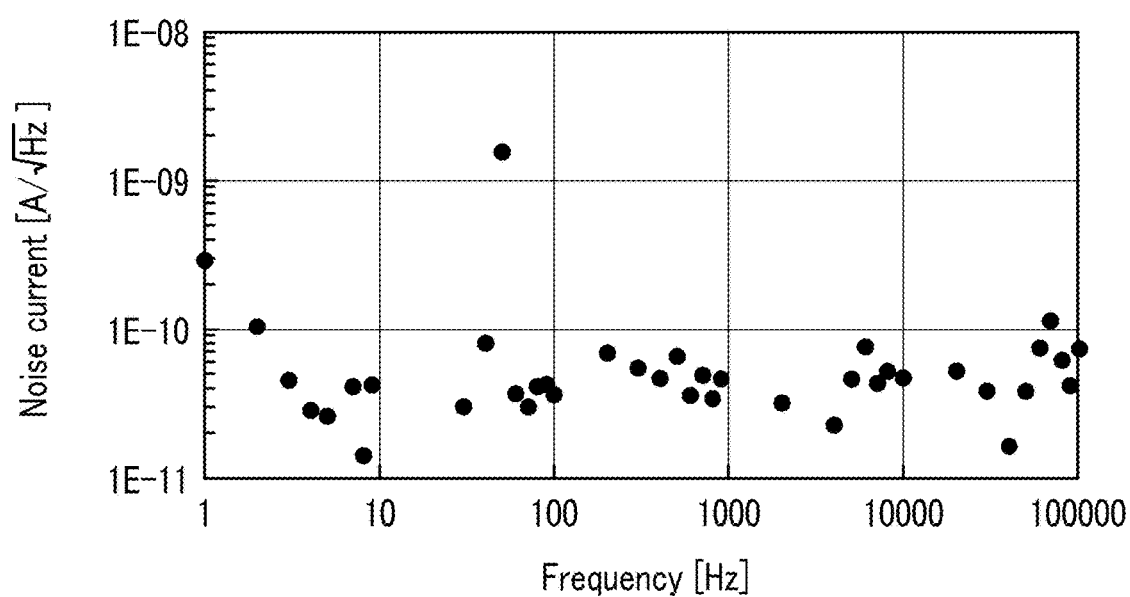
FIG. 8 is a chart showing noise currents of the terahertz wave detection device according to the present embodiment.

FIG. 8 is a chart showing noise currents of the terahertz wave detection device 10. As shown in FIG. 8, the excellent detection sensitivity of a noise current being $10^{-10}$ to $10^{-11}$ $A/Hz^{1/2}$ in the extremely wide frequency band, from sub THz to several tens THz, was obtained. The device operates as an excellent low noise detector.

Figure 9A:
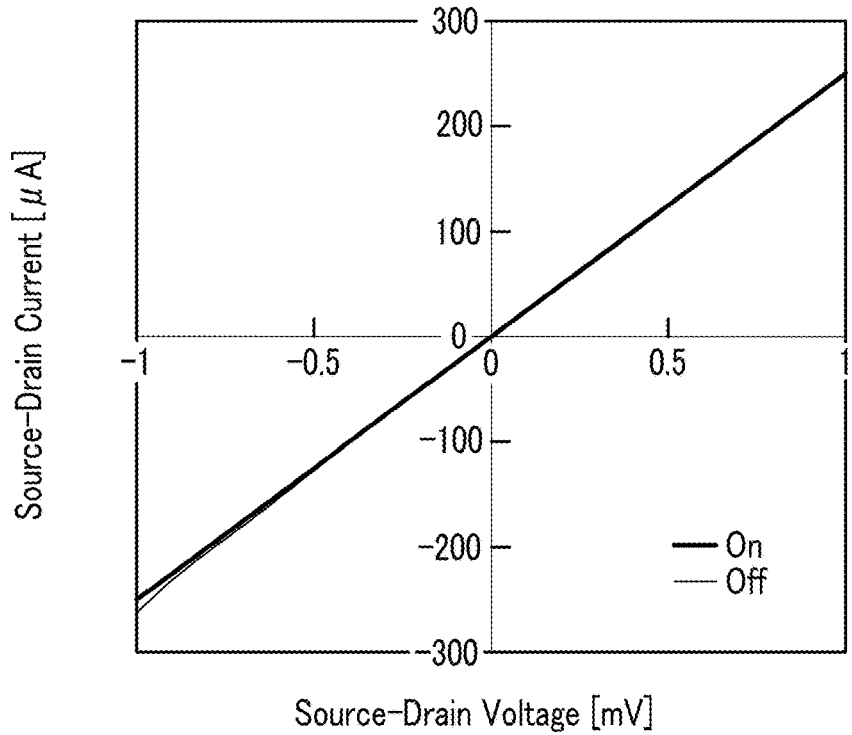
FIG. 9A is a chart showing the response to THz waves, as the I-V characteristics, in a comparative case using the same kind of metal (Au—Au) for a first electrode (source electrode) and a second electrode (drain electrode)
Figure 9B:
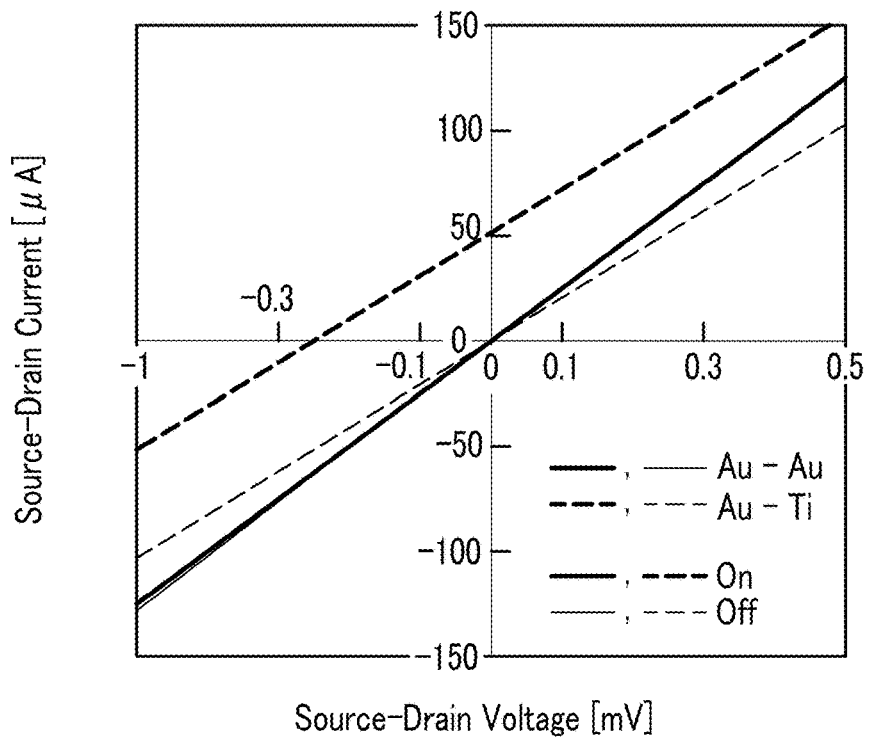
FIG. 9B is a chart showing the response to THz waves, as the I-V characteristics, in the present embodiment using Au, having high thermal conductivity, for the first electrode (source electrode) and Ti, having low thermal conductivity, for the second electrode (drain electrode)

FIGS. 9A to 9B are charts showing the response to THz waves (under room temperature), as the I-V characteristics, of the terahertz wave detection device 10 in a comparative case and the present embodiment. The horizontal axis indicates source-drain voltage [mV] and the vertical axis indicates source-drain current [μA]. The thin solid line and thin broken line of the I-V characteristics in FIGS. 9A and 9B indicate the case having no irradiation with THz waves (Off), and the thick solid line and the thick broken line indicate the case having irradiation with THz waves (On). FIG. 9A shows a case using the same metal (Au—Au) for the first electrode 12 (source electrode) and the second electrode 13 (drain electrode). As shown in FIG. 9A, no shift of the I-V characteristics due to irradiation with THz waves is observed in the case. FIG. 9B shows a case using Au, having high thermal conductivity, for the first electrode 12 (source electrode) and Ti, having low thermal conductivity, for the second electrode 13 (source electrode). As shown in FIG. 9B, the I-V characteristics was linear when the THz wave was irradiated, and a shift of the I-V characteristics was observed. When the combination of (Au—Ti) is used, the shift of the I-V characteristics is the largest. As described above, the terahertz wave detection device 10 has been produced that has broadband operating in the entire region of the THz band, has high sensitivity, and is compact, in the case using electrodes having the same thermal conductivity or different thermal conductivities.

Next are examples of checking objects using an 8-element array sensor (flexible array sensor 30) (hereinafter referred to as an 8-element array sensor 30) prototyped with the above-described optimum values. A description will be given of results of imaging (one-dimensional scan) in the THz band.

Case of Using 8-Element Array Sensor 30 Laid Flat

FIG. 10 illustrates an overall checking system using the 8-element array sensor 30 laid flat. As shown in FIG. 10, a metal mask 52 (sample), as an inspected object, is irradiated with THz waves 40 in the infrared region (IR irradiation) from above. The THz waves are generated by a femtosecond laser or the like. The metal mask 52 is formed such that information 54 (here, characters X, Y, Z) is marked on an aluminum foil (non-transmissive of THz waves) 53 on which an opaque (non-transmissive of visible light) film (transmissive of THz waves) is then overlaid. The 8-element array sensor 30 is disposed under the metal mask 52 and is moved in an X-Y plane (i.e., two-dimensionally) with respect to the metal mask 52. Alternatively, as shown in FIG. 10, the 8-element array sensor 30 is disposed and then the metal mask 52 may be moved in the arrowed direction in FIG. 10 while being irradiated with the THz waves 40 in the infrared region from above. That is, the 8-element array sensor 30 is relatively moved in one direction to cross the waves to observe a two-dimensional image.

Figure 11A:
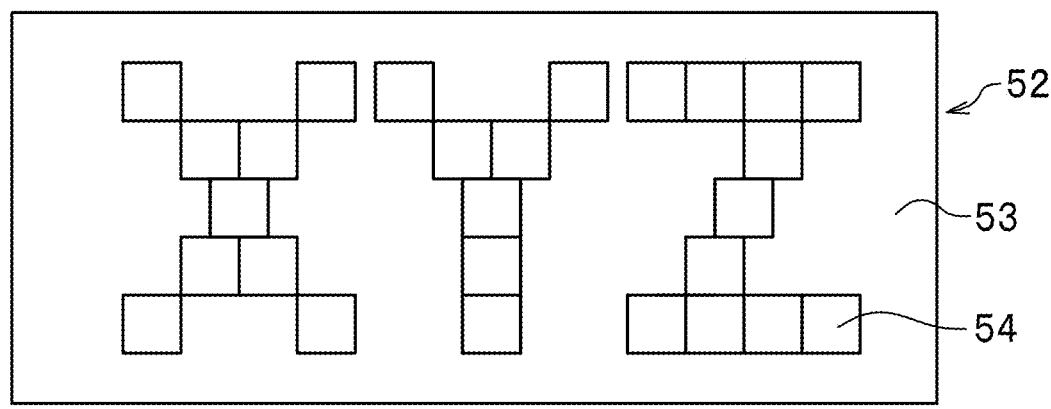
FIG. 11A illustrates a sample, as viewed from below, observed in the checking system in FIG. 10.
Figure 11B:
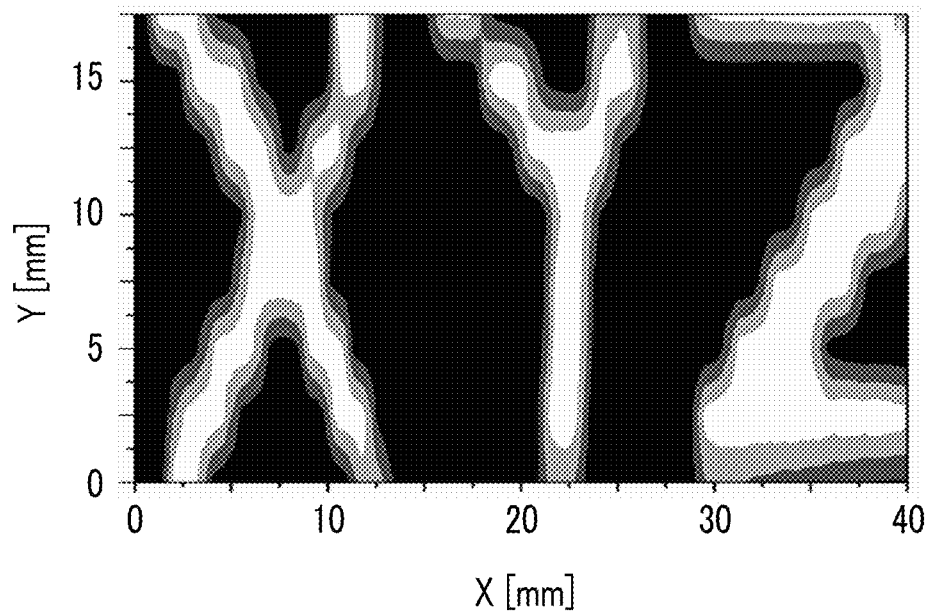
FIG. 11B illustrates an image of the sample, through transmitted THz waves, observed in the checking system in FIG. 10.

FIGS. 11A and 11B illustrate a case of observation in the checking system in FIG. 10, where FIG. 11A illustrates a sample as viewed from below and FIG. 11B illustrates an observed image, through transmitted THz waves, of the sample. As shown in FIG. 11A, the metal mask 52 (sample) is formed with the characters 54 (X, Y, Z) marked on the aluminum foil 55 (character portions are cut out of the aluminum foil, for example). The 8-element array sensor 30 is moved in one direction to observe a two-dimensional image, as shown in FIG. 10. The characters 54 of the metal mask 52 were observed with high sensitivity and high accuracy, as shown in FIG. 11B. As the terahertz wave detection elements 10 are arrayed, a two-dimensional image is obtained merely with the 8-element array sensor 30 being moved in one direction. This allows for observation at high speed.

Figure 12A:
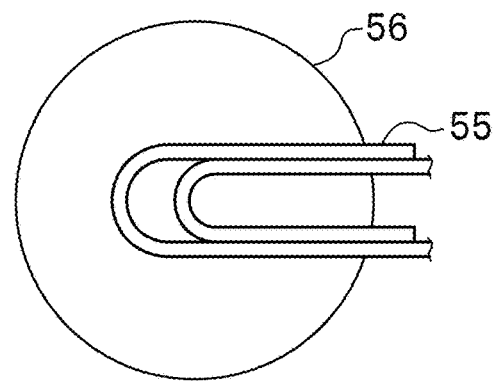
FIG. 12A illustrates another sample, as viewed from below, observed in the checking system in FIG. 10.
Figure 12B:
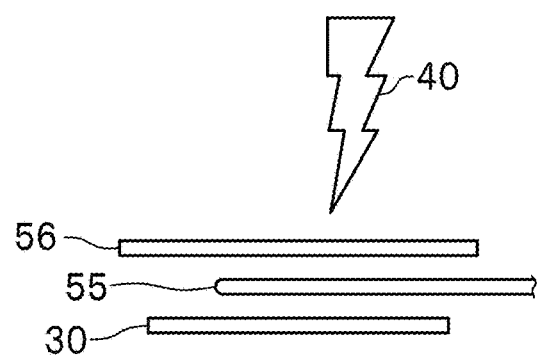
FIG. 12B illustrates said another sample, in a lateral view, observed in the checking system in FIG. 10.
Figure 12C:
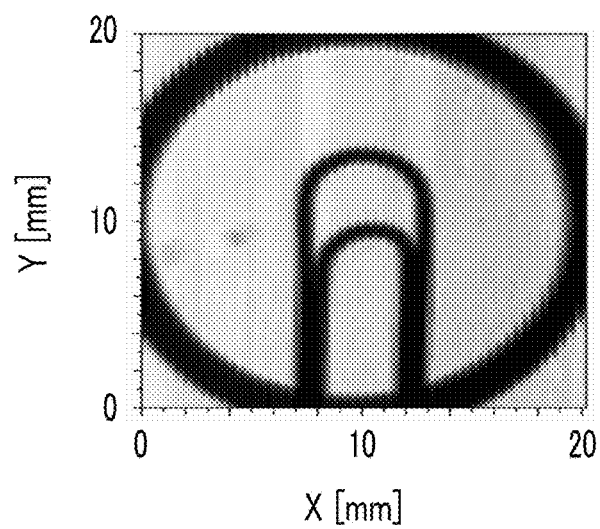
FIG. 12C illustrates an image of said another sample, through transmitted THz waves, observed in the checking system in FIG. 10.

FIGS. 12A to 12C illustrate a case of observing another sample in the checking system in FIG. 10, where FIG. 12A illustrates said another sample as viewed from below, FIG. 12B illustrates said another example in a lateral view, and FIG. 12C illustrates an observed image, through transmitted THz waves, of said another sample. A part of the clip (soft iron) 55 (sample) is covered with a circular Ge plate 56, as shown in FIG. 12A. Here, Ge of the Ge plate 56 transmits THz waves. The Fe of the clip 55 does not transmit THz waves. When viewed from above, the clip 55 (sample) is hidden by the Ge plate 56 and therefore invisible. That is, visible light cannot detect what is hidden behind the shield. The 8-element array sensor 30 utilizes transmissive property of the THz wave to clearly detect the metal (clip 55) hidden behind the shield as with the transmissive image in FIG. 12C. The 8-element array sensor 30 is moved in one direction to observe a two-dimensional image, as shown in FIG. 10. The clip 55 was observed with high sensitivity and high accuracy, as shown in FIG. 12C. As the terahertz wave detection elements 10 are arrayed, a two-dimensional image is obtained merely with the 8-element array sensor 30 being moved in one direction to cross the waves. This allows for observation at high speed.

Case of 23-Element Array Sensor 30A Being Curvedly Arranged

Figure 13A:
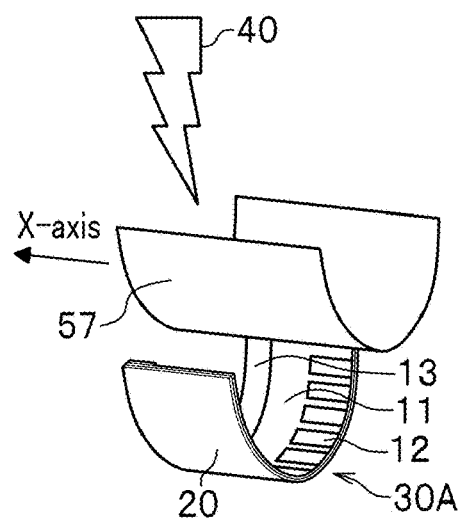
FIG. 13A illustrates an overall checking system using a curved terahertz wave detection device of the present embodiment.
Figure 13B:
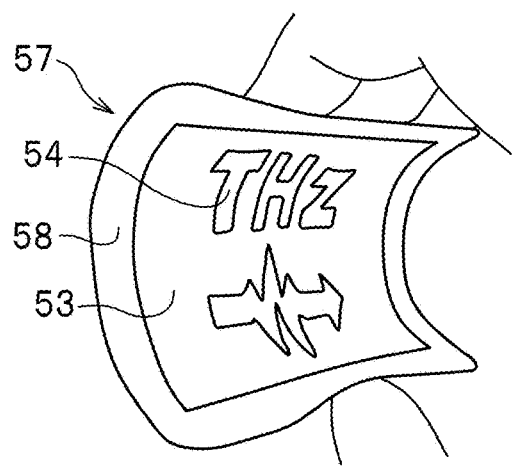
FIG. 13B illustrates a case of a bent mask being checked in the checking system in FIG. 13A.
Figure 13C:
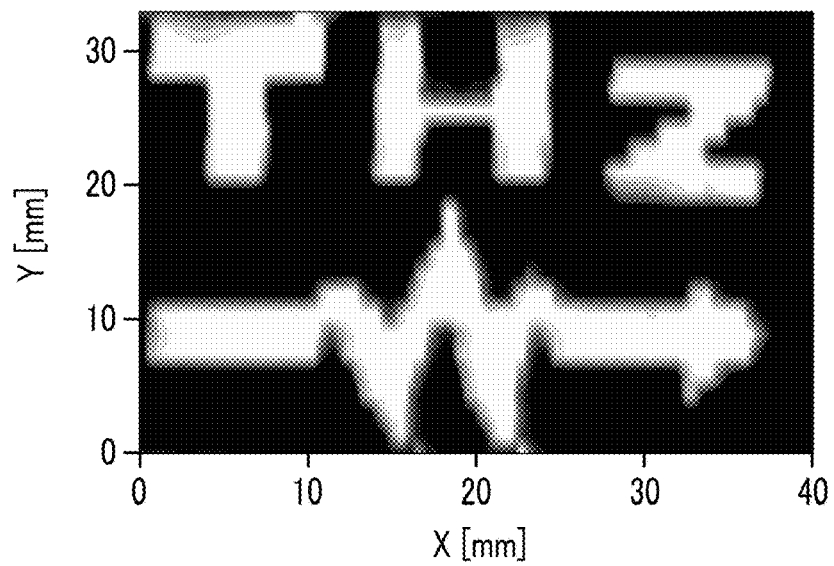
FIG. 13C illustrates a two-dimensional image of the sample observed in the checking system in FIG. 13A.

FIGS. 13A to 13C illustrate an overall checking system having a 23-element array sensor 30A (flexible array sensor 30) (hereinafter referred to as the 23-element array sensor 30A) curved. As shown in FIG. 13A, the 23-element array detector 30A has the 23 terahertz wave detection elements 10 arrayed on the flexible substrate 20. The material of the flexible substrate 20 may be any material such as a polyimide film. The single-walled carbon nanotube film 11 (see FIGS. 1A and 1B) has high electrical conductivity and mechanical strength, so as to be used as the flexible substrate 20 which is flexible. The 23-element array sensor 30A is a flexible sensor having the 23 terahertz wave detection elements 10, each having a width of 1 mm, arrayed on the flexible substrates 20 at intervals of 0.5 mm. The 23-element array sensor 30A may be worn so as to be in close contact with a curved part on a living body such as a finger and an arm (see FIG. 14 to be described below).

As shown in FIG. 13B, the information 54 (here, characters X, Y, Z and a graphic) is marked on an aluminum foil (non-transmissive of THz waves) 55 on which an opaque (non-transmissive of visible light) film (transmissive of THz waves) 58 is then overlaid, to form a flexible bent mask 57. The bent mask 57 (sample) is irradiated with the THz waves 40 in the infrared region from above. The THz waves are generated by a femtosecond laser or the like. The bent mask 57 (sample) is moved in the arrowed direction, while being irradiated with the THz waves 40 from above, to observe a two-dimensional image, as shown in FIG. 13A. When the bent mask 57 is moved in one direction to observe a two-dimensional image, the characters and graphic 54 of the bent mask 57 were observed with high sensitivity and high accuracy, as shown in FIG. 13C. Even when the checked objects were curved ones, clear images were obtained. As the terahertz wave detection elements 10 are arrayed, a two-dimensional image is obtained merely with the 23-element array sensor 30A being moved in one direction. This allows for observation at high speed.

Case of 23-Element Array Sensor 30A Wound Around Hand (Passive Imaging)

Figure 14A:
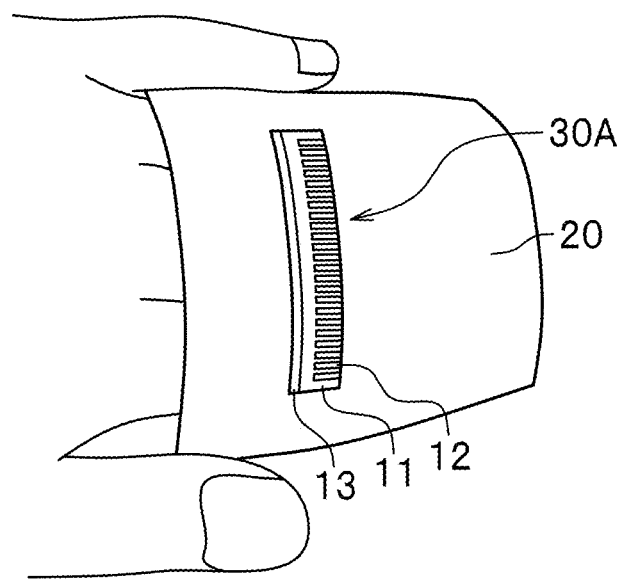
FIG. 14A illustrates an application case when a 23-element array sensor, as the terahertz wave detection device of the present embodiment, is disposed on a flexible substrate.
Figure 14B:
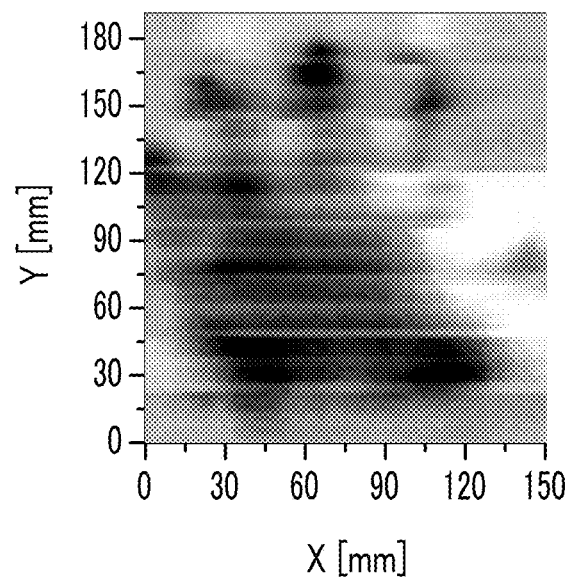
FIG. 14B is a chart showing an image of the sample, through transmitted THz waves, observed in the case shown in FIG. 14A.

Hereinbelow, a description will be given of application cases of omnidirectional inspection using the flexible array sensor 30, with reference to FIGS. 14A to 22. A case of the 23-element array sensor 30A wound around a hand has characteristics of 1) a scan by flexible THz waves (scan by curving THz waves) from the viewpoint of checking a curved object, 2) a biotic scan from the viewpoint of checking a human body, and 3) passive imaging to check an object with no light source. FIGS. 14A and 14B illustrate an application case of the 23-element array sensor 30A being wound around a hand (passive imaging, i.e., to check THz waves from a checked object without using any light/wave source). FIG. 14A illustrates an application case when the 23-element array sensor 30A is wound around a hand and FIG. 14B is a chart showing an observed image through transmitted THz waves. As shown in FIG. 14B, a clear image is obtained even when the checked object is a curved hand. In addition, as a result of checking through a biotic scan, thermal radiation from the hand is sensed to execute imaging even in the absence of any light/wave source. In this way, passive imaging through radiation from the hand was observed with no external light/wave source. This is a promising feature for medical applications such as medical care sensors.

Flexible Imaging of Curved Samples

Figure 15A:
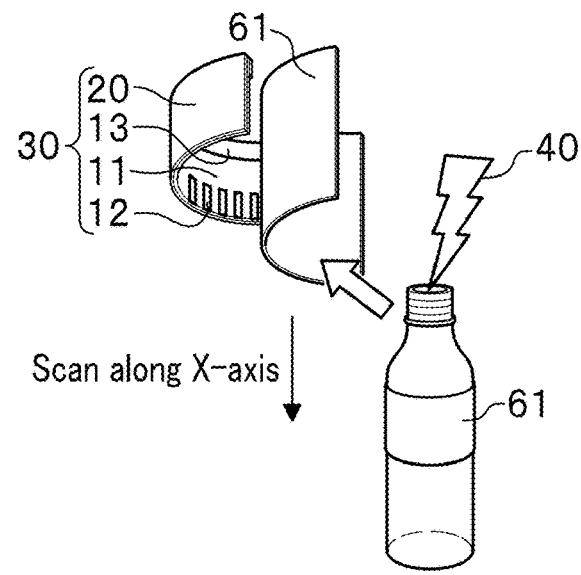
FIG. 15A illustrates a case of observing a curved sample, in a checking system using a flexible array sensor, with flexible imaging by the terahertz wave detection device according to the present embodiment.
Figure 15B:
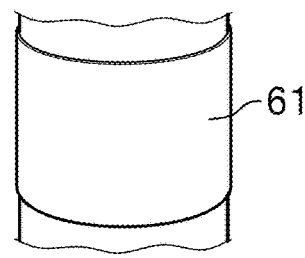
FIG. 15B is a cutout of a core portion of a PET bottle, as a curved sample, as viewed from the front, observed in the checking system in FIG. 15A.
Figure 15C:
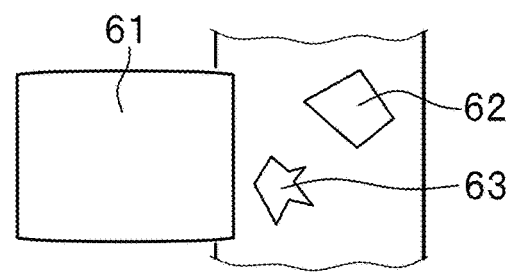
FIG. 15C illustrates foreign matter and the like, inside a label, observed in the checking system in FIG. 15A.
Figure 16:
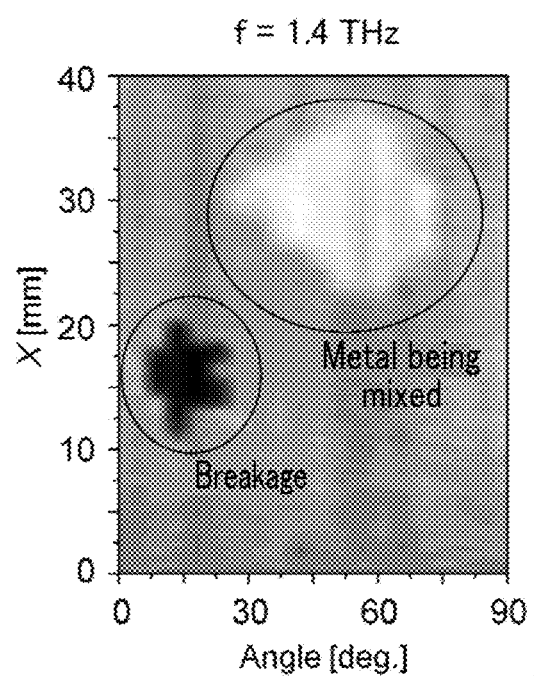
FIG. 16 is a chart showing an image, through transmitted THz waves, observed in the checking system in FIG. 15A.

FIGS. 15A to 15C illustrate flexible imaging of a curved sample, where FIG. 15A illustrates a case of observing a curved sample in a checking system using the flexible array sensor 30, FIG. 15B is a cutout of a core portion of a PET bottle as a curved sample as viewed from the front, and GIG. 15C illustrates foreign matter and the like inside a label. FIG. 16 is a chart showing an observed image, through transmitted THz waves, observed in the checking system in FIG. 15A. As shown in FIG. 15A, the flexible array sensor 30 is moved in the arrowed direction (downward) while a label 61 of the PET bottle, as a checked object, being irradiated with THz waves 40 (transmitted THz waves) from inside of the PET bottle, to observe a two-dimensional image. As the flexible array sensor 30 has the terahertz wave detection elements 10 arrayed therein, a two-dimensional image is obtained merely with the flexible array sensor 30 being moved downward. As shown in FIG. 15B, a state under the label 61 cannot be seen with the naked eye. In reality, metallic foreign matter 62 is mingled under the label 61 and the PET bottle has a breakage 63, as shown in FIG. 15C. The flexible array sensor 30 clearly detects metallic foreign matter and a breakage hidden behind the label 61, as in the transmitted image in FIG. 16, through irradiation with THz waves 40 of 1.4 THz, for example.

Omnidirectional Flexible Imaging of Curved Samples

Figure 18A:
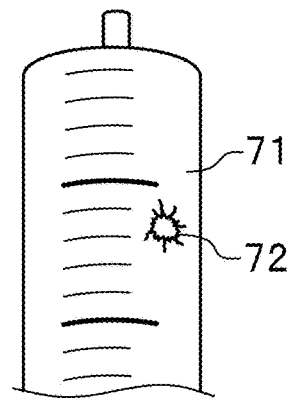
FIG. 18A indicates a breakage of the curved sample (syringe) to be observed by the terahertz wave detection device according to the present embodiment.
Figure 18B:
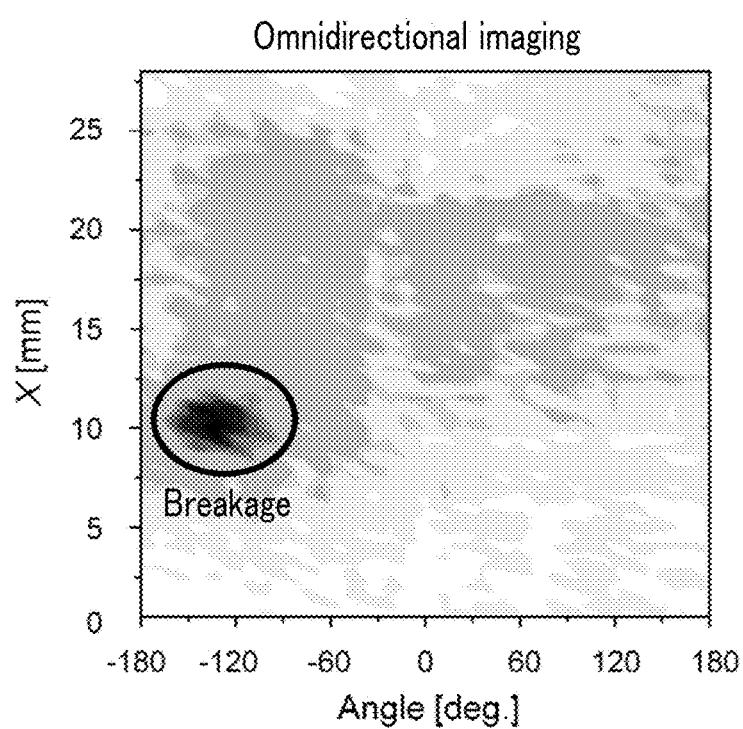
FIG. 18B is a chart showing an image of the curved sample (syringe) observed by the terahertz wave detection device according to the present embodiment through omnidirectional flexible imaging for breakage detection.

FIG. 17 illustrates omnidirectional flexible imaging of a curved sample (syringe) in a checking system using the flexible array sensor 30. FIGS. 18A and 18B show a breakage of a curved sample (syringe), where FIG. 18A indicates a breakage of the syringe and FIG. 18B is a chart showing an observed image through omnidirectional imaging. As shown in FIG. 17, the flexible array sensor 30 curved in an annular shape is used to scan through a medical device (syringe 71) to be checked in the X-axis direction (vertical direction). As the flexible array sensor 30 is curved over the entire circumference about the X-axis, scanning in the X-axis direction with the flexible array sensor 30 makes a multi-view scan of the entire circumference scanned at one time. If there is a breakage 72 in the syringe 71, as shown in FIG. 18A, the breakage is shown in the observed image through the omnidirectional imaging in FIG. 18B. The flexible array sensor 30 allows for omnidirectional inspection without using a large checking system. Accordingly, the flexible array sensor 30 has great advantages over existing THz wave detectors.

Multi-View Scan

<Configuration with THz Wave Source>

Figure 19:
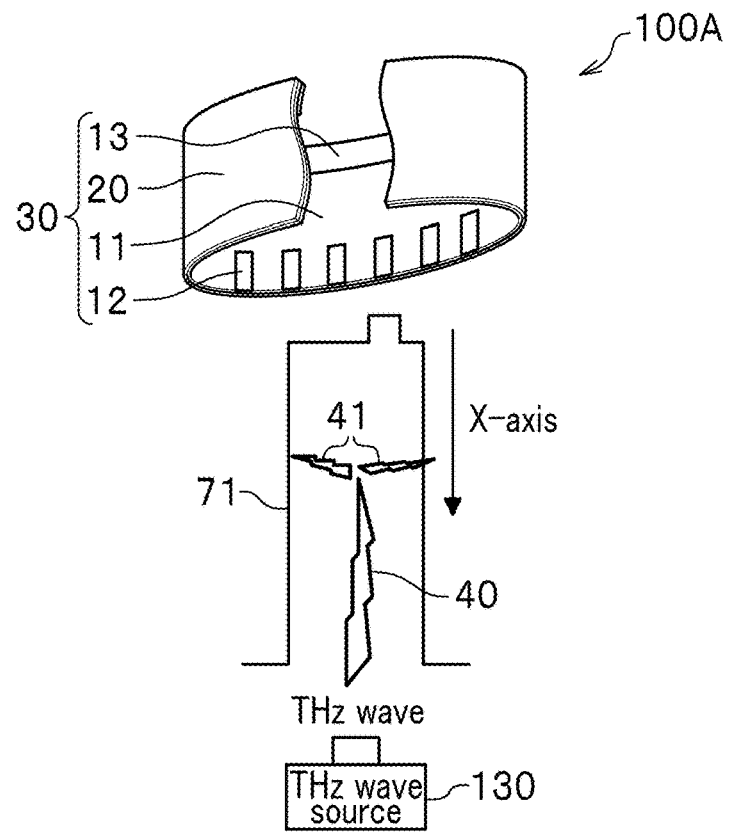
FIG. 19 illustrates a checking system using a flexible array sensor as the terahertz wave detection device according to the present embodiment.

Next, a description will be given of specific examples of multi-view scan, with reference to FIGS. 19 to 22. FIG. 19 illustrates a checking system using the flexible array sensor 30. The same components as those in FIGS. 1 and 17 are denoted by the same reference numerals. A terahertz wave detection system 100A includes a THz wave source 130, as shown in FIG. 19. The THz wave source 130 is arranged on the X-axis of a checked medical device (syringe 71) to irradiate the inside of the syringe 71 (into the checked object) with the THz waves 40 of 1.4 THz, for example. In this configuration, the inside of the syringe 71 is irradiated with the THz waves 40 to have the THz waves 40 subjected to diffuse reflection 41 inside the syringe 71. In this state, the flexible array sensor 30 in an annular shape is made to pass through the checked medical instrument (syringe 71) in the X-axis direction. As the flexible array sensor 30 is curved around the entire circumference about the X-axis, scanning by the flexible array sensor 30 in the X-axis direction achieves multi-view scanning. The multi-view scan configuration in FIG. 19 is effective when one THz wave source 130 is arranged. This is active imaging using the THz wave source 130, but a THz wave source suitable for a checked object can be used. This allows for enhancing the definition (resolution) of inspection to execute more accurate omnidirectional inspection.

<Configuration with THz Wave Source Incorporated into Scanner>

Figure 20:
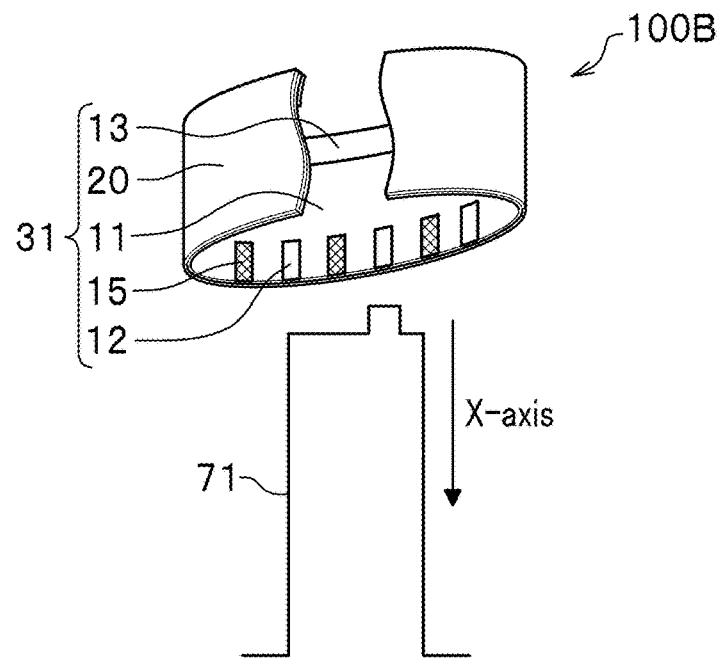
FIG. 20 illustrates a checking system using a flexible array sensor as the terahertz wave detection device according to the present embodiment, which has a THz oscillator incorporated therein.

FIG. 20 illustrates a checking system in which a THz oscillator is incorporated into a flexible array sensor 31. The same components as those in FIG. 17 are denoted by the same reference numerals. As shown in FIG. 20, the flexible array sensor 31 in a terahertz wave detection system 100B includes a plurality of terahertz wave detection elements (terahertz wave detection device), each having the single-walled carbon nanotube film 11, the first electrode 12, and the second electrode 13, and a plurality of THz oscillators 15. Each of the plurality of terahertz wave detection elements is a THz wave receiver that receives THz waves from the THz oscillator 15. In the present embodiment, the terahertz wave detection elements and the THz oscillators 15 are alternately arranged over the entire circumference of the flexible array sensor 31. For example, if there are "n" (which is an arbitrary natural number) THz wave detection elements, there are "n" THz oscillators. Note that the number, and arrangement, of the terahertz wave detection elements 10 and the THz oscillators 15 are not limited. Besides, the correspondence relationship between the terahertz wave detection element 10 and the THz oscillator 15 is not limited to 1 to 1 and may be 1 to "m" (where "m" is an arbitrary natural number), where one THz oscillator 15 corresponds to "m" terahertz wave detection elements 10.

In this configuration, the THz oscillators 15 transmit THz waves, while the terahertz wave detection elements 10 check the THz waves transmitted by the THz oscillators 15. As the flexible array sensor 31 is curved around the entire circumference about the X-axis, moving the flexible array sensor 31 in the X-axis direction achieves multi-view scanning.

The multi-view scan configuration in FIG. 20 is effective when the THz wave source and the terahertz wave detection elements 10 are combined together for checking in a compact manner. For example, the configuration requires no THz wave source 130 installed on the X-axis of the checked medical device (syringe 71), as in FIG. 19. This allows the entire terahertz wave detection system 100B to be reduced in size. Besides, as the THz wave source 130 is not required, checking through THz waves is more easily executed using the flexible array sensor 31. That is, the omnidirectional inspection is achieved merely with the flexible array sensor 31 being passed through around a checked object, without the THz wave source 130. For example, the flexible array sensor 31 may be arranged in an inspection process line to inspect a checked object passing through the flexible array sensor 31 in a short time, so that productivity is improved. Also, this is active imaging and a THz wave source suitable for a checked object can be used, to allow for enhancing the definition (resolution) of inspection to execute more accurate omnidirectional inspection, as with the case in FIG. 19.

<Configuration without THz Oscillator>

Figure 21:
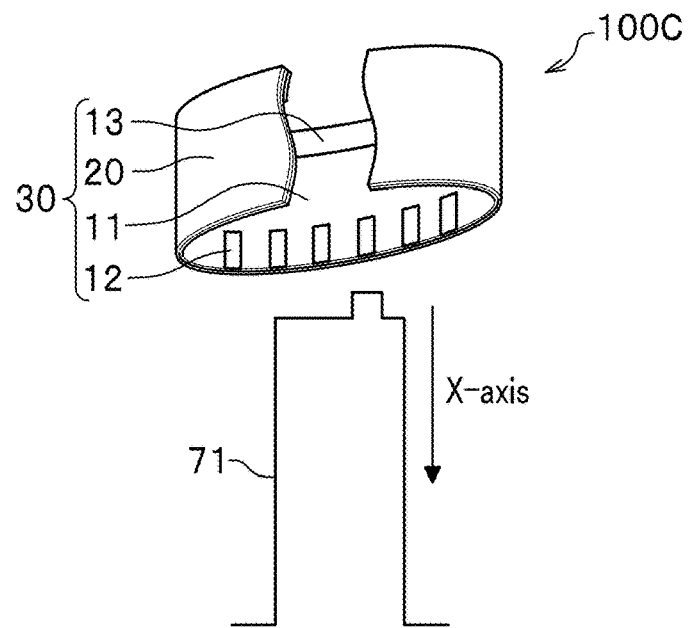
FIG. 21 illustrates a checking system using a flexible array sensor as the terahertz wave detection device according to the present embodiment.

FIG. 21 illustrates a checking system using the flexible array sensor 30. The same components as those in FIG. 17 are denoted by the same reference numerals. As shown in FIG. 21, a terahertz wave detection system 100C does not include a THz oscillator. For example, the flexible array sensor 30 in FIG. 1 may be used alone, the THz wave source 130 may be removed from the terahertz wave detection system 100A in FIG. 19, or the THz oscillator 15 of the flexible array sensor 31 in the terahertz wave detection system 100B in FIG. 20 may be deactivated. The configuration for multi-view scan in FIG. 21 is capable of inspecting the checked medical device (syringe 71) through passive imaging of THz waves emitted therefrom, with no THz oscillator (with no external wave source). This is effective when the influence from irradiation by a THz wave source is desired to be avoided.

Hereinabove, the description has been given of omnidirectional flexible imaging to scan an object over the entire circumference about the X-axis thereof. Omnidirectional flexible imaging may be applied to the polar coordinates system. A description will be given of breast cancer inspection using THz waves as omnidirectional flexible imaging in the polar coordinate system.

<Configuration with THz Wave Source Incorporated into Scanner: Biotic Scan>

Figure 22:
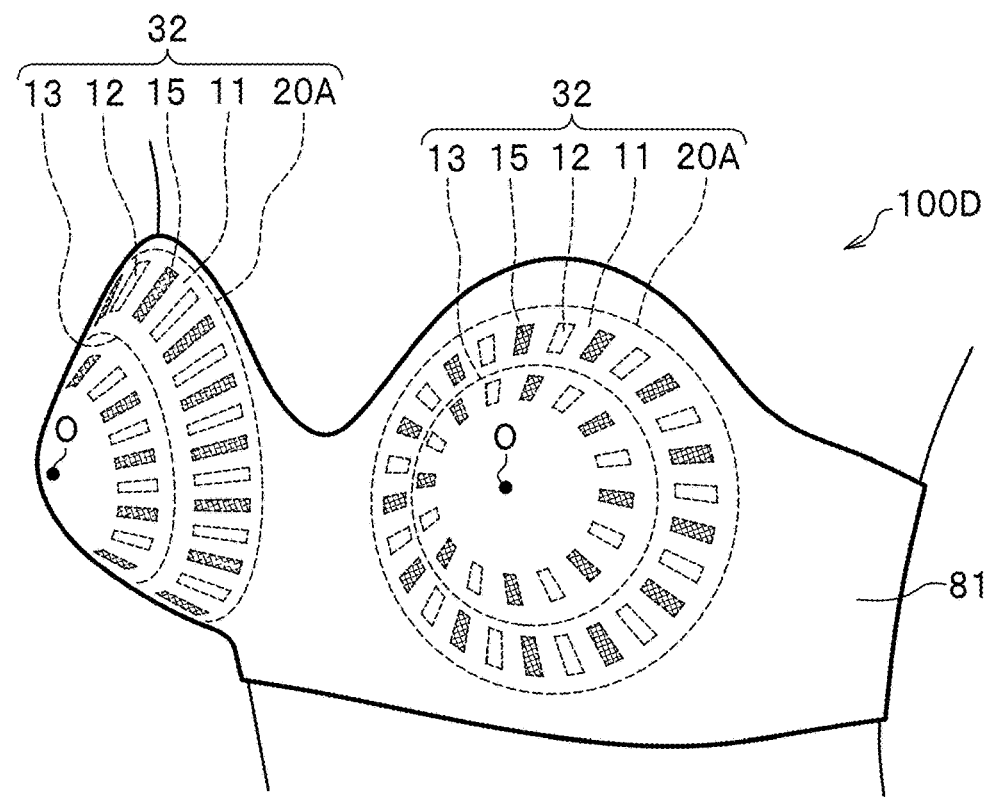
FIG. 22 illustrates a case of a flexible array sensor as the terahertz wave detection device according to the present embodiment, being applied to a breast cancer inspection device.

The incidence of breast cancer (National Estimates in 2011) accounts for approximately 20% of all cancer cases among women. It is important in breast cancer screening to find a breast cancer easily with high sensitivity. FIG. 22 illustrates a case of a flexible array sensor 32 being applied to a breast cancer inspection device. The same components as those in FIG. 17 are denoted by the same reference numerals. As shown in FIG. 22, the flexible array sensor 32 of a terahertz wave detection system 100D is applied to a breast cancer inspection device. A pair of right and left flexible array sensors 32 is arranged on an attachment device 81 to be attached to the chest. The flexible array sensor 32 includes the terahertz wave detection elements (terahertz wave detection devices), each having the single-walled carbon nanotube film 11, the first electrode 12, and the second electrode 13, and the THz oscillators 15, which are arranged in a plurality of rows concentrically about the vertex O, and a flexible substrate 20A having the terahertz wave detection elements 10 and the THz oscillators 15 fixed thereon in a curved shape (cup shape) as being convex upward. The terahertz wave detection element 10 detects 1.7-THz waves which has a property of being significantly absorbed into a breast cancer. The THz oscillator 15 emits THz waves to which a breast cancer significantly responds.

As the flexible array sensor 32 has the terahertz wave detection elements arranged concentrically around the vertex O in this configuration, the multi-view scan in the polar coordinate system is achieved merely with the attachment device 81 being attached to the chest. Results of the examination can be used to diagnose a breast cancer. This is an active imaging using the THz oscillators 15, but a THz wave source suitable for a checked object can be used. This allows for enhancing the definition (resolution) of examination to execute more accurate omnidirectional inspection. In addition, as the flexible array sensor 32 is closely contacted with the skin of the subject, a clear image is obtained even when the checked object is a curved breast. Note that imaging may be executed without the THz oscillators 15, because the flexible array sensor 32 is closely contacted with the skin of the subject to suitably detect thermal emission from the skin of the subject. If passive imaging of emission from the skin is observed with no external wave source, this is a promising feature for medical applications such as medical care sensors.

<Flexible Imaging System>

Figure 23A:
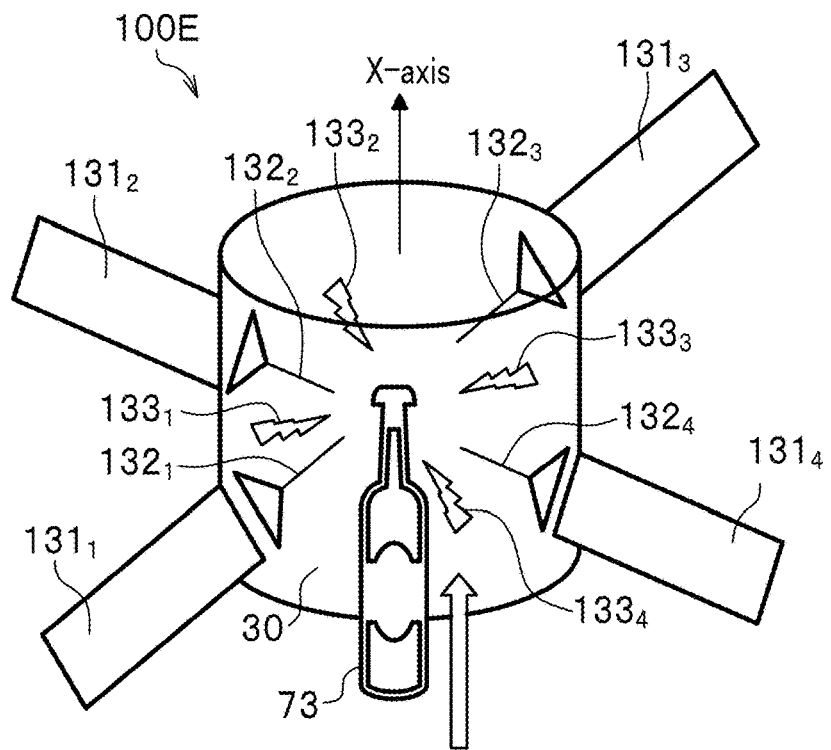
FIG. 23A illustrates an imaging system using a flexible array sensor as the terahertz wave detection device according to the present embodiment.

FIG. 23A illustrates an imaging system using the flexible array sensor 30. The same components as those in FIGS. 1 and 19 are denoted by the same reference numerals. A terahertz wave detection system 100E includes THz laser devices $131_1$ to $131_4$ (terahertz oscillators), as shown in FIG. 23A. A plurality (four in this case) of THz laser devices $131_1$ to $131_4$ are arranged on the outer peripheral surface of the annular flexible array sensor 30.

In this configuration, an imaged object 73 is inserted into the flexible array sensor 30. The imaged object 73 is irradiated with THz waves $132_1$ to $132_4$ by the THz laser devices $131_1$ to $131_4$ from four directions, to cause the THz waves $132_1$ to $132_4$ to have diffused reflections $133_1$ to $133_4$ in the flexible array sensor 30. As the flexible array sensor 30 is curved over the entire circumference about the X-axis, the flexible array sensor 30 detects THz waves of the diffused reflections $133_1$ to $133_4$ when the imaged object 73 passes through, to achieve omnidirectional imaging.

Figure 23B:
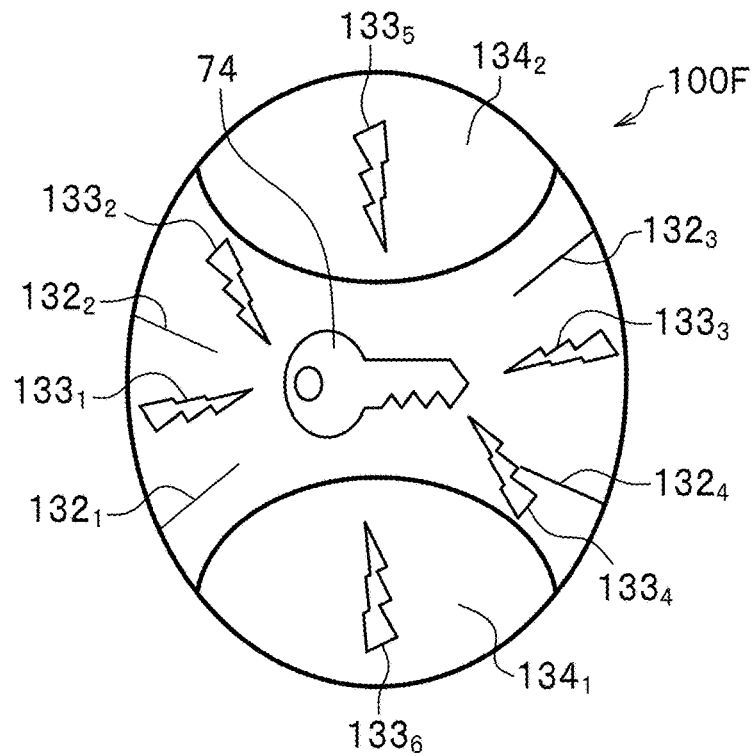
FIG. 23B illustrates another imaging system using a flexible array sensor as the terahertz wave detection device according to the present embodiment.

FIG. 23B illustrates another imaging system using the flexible array sensor 30. The same components as those in FIG. 23A are denoted by the same reference numerals. A terahertz wave detection system 100F further includes ball cameras $134_1$ and $134_2$, as shown in FIG. 23B. In this configuration, an imaged object 74 is placed in the terahertz wave detection system 100F and irradiated with the THz waves $132_1$ to $132_4$ by the THz laser devices $131_1$ to $131_4$ (not shown) from four directions, to cause the THz waves to have diffused reflections $133_1$ to $133_6$ inside the flexible array sensor 30. The ball cameras $134_1$ and $134_2$ capture the diffused reflections $133_5$ to $133_6$ with a 360-degree field of vision. This achieves 3D imaging in addition to omnidirectional imaging.

<Wearable Medical Tester>

Figure 24A:
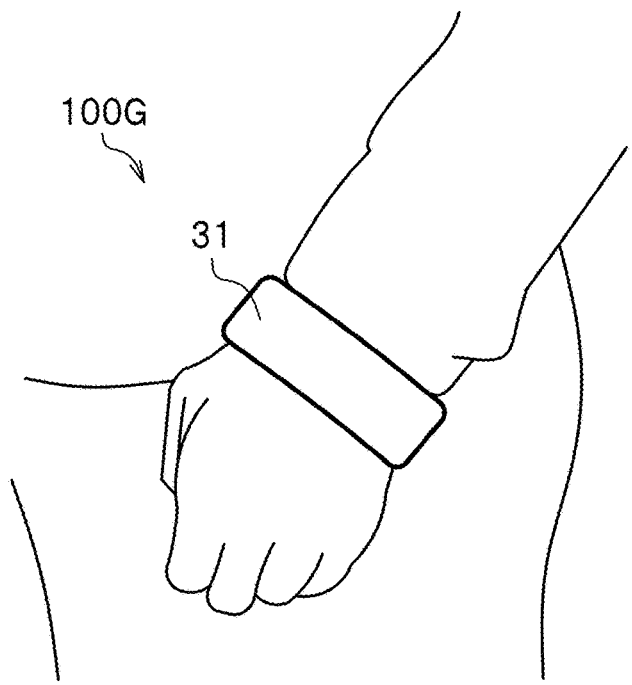
FIG. 24A illustrates a case of wearing a wearable medical tester using a flexible array sensor as the terahertz wave detection device according to the present embodiment.
Figure 24B:
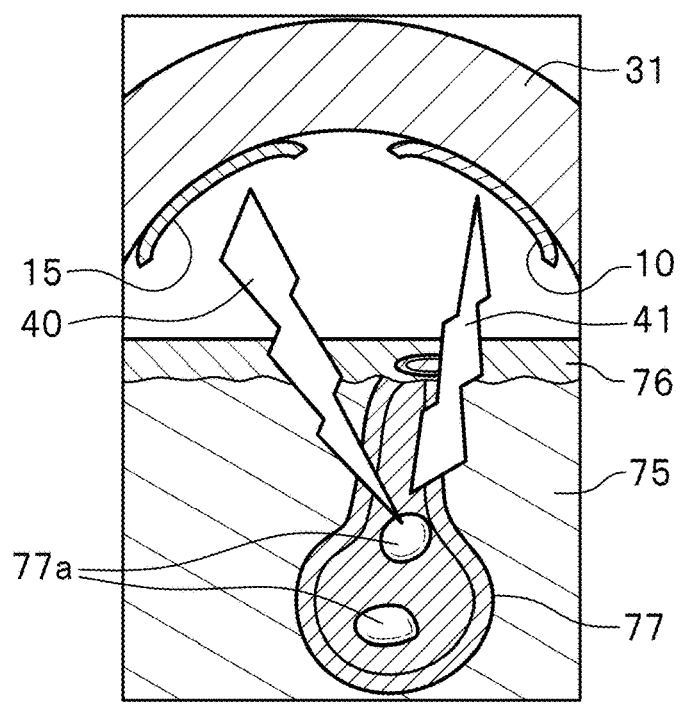
FIG. 24B is an image chart to show an example checked by the terahertz wave detection device according to the present embodiment.

FIGS. 24A to 24B show a wearable medical tester using the flexible array sensor 31, where FIG. 24A illustrates a case of wearing the wearable medical tester and FIG. 24B is an image chart to show an example checked thereby. The same components as those in FIG. 20 are denoted by the same reference numerals. A terahertz wave detection system 100G (wearable medical tester) has the flexible array sensor 31 wound around the wrist of a subject, as shown in FIG. 24A. The flexible array sensor 31 includes a plurality of the terahertz wave detection elements 10 and a plurality of the THz oscillators 15, as shown in FIG. 24B. The wrist having the flexible array sensor 31 wound therearound includes, on the subcutaneous tissue, a dermis 75, an epidermis 76 on the dermis 75, a sweat gland 77 in the dermis 75 near the subcutaneous tissue, and a sweat hole 78 (not shown) to discharge sweat 77a formed by the sweat gland 77.

In this configuration, the THz oscillator 15 of the flexible array sensor 31 emits the THz wave 40 and the terahertz wave detection element 10 checks a reflected wave (reflected THz wave) 41 of the THz wave 40 emitted by the THz oscillator 15, as shown in FIG. 24B. An apocrine gland secretes sweat due to stress and excitement. In addition, the human body's sweat 77a has electromagnetic resonance absorption in the THz range. The terahertz wave detection system 100G (wearable medical tester) has the flexible array sensor 31 worn on the wrist of the subject to image the sweat 77a under the skin, non-invasively in real time, by the terahertz wave detection elements 10, as shown in FIG. 24A. Such an image may be transferred to a hospital by wireless, for example, so that conditions of the subject are perceived in real time.

The above-described embodiments have dealt with the cases where the flexible array sensor is disposed to surround the outside of the object. However, the flexible array sensor can be placed at any relative position to the object. For example, the flexible array sensor may be placed inside an object to image THz waves.

Figure 25:
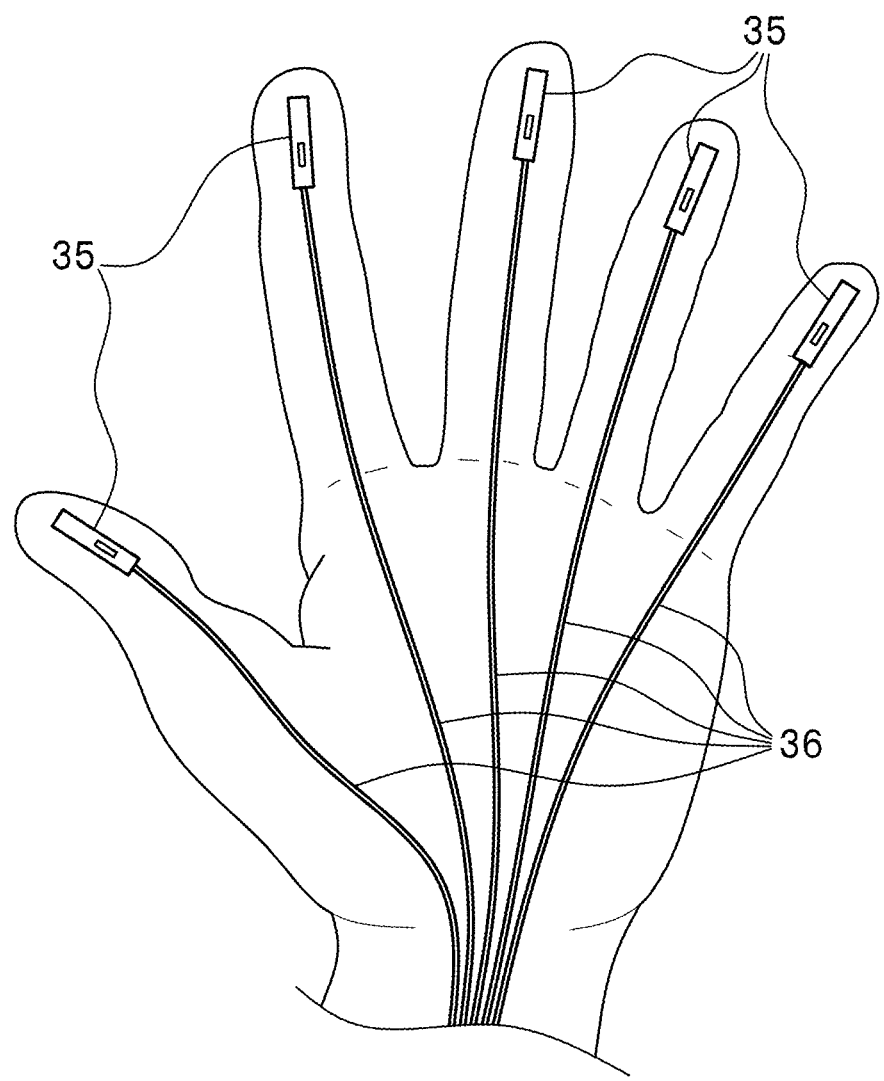
FIG. 25 illustrates a case of wearing flexible array sensors as the terahertz wave detection devices according to the present embodiment, on fingers.

FIG. 25 illustrates a case of flexible array sensors, as the terahertz wave detection devices according to the present embodiment, being worn on fingers. Flexible array sensors 35 (terahertz wave detection devices) are worn on fingers with medical tape wound therearound, for example, as shown in FIG. 25. Signal line wires 36 from the flexible array sensors 35 are bundled on a wrist or the like and connected to a checking device (not shown). In this case, the signal line wire 36 may be connected to a wireless device to transmit data wirelessly, such as using a Bluetooth (registered trademark) protocol.

Figure 26A:
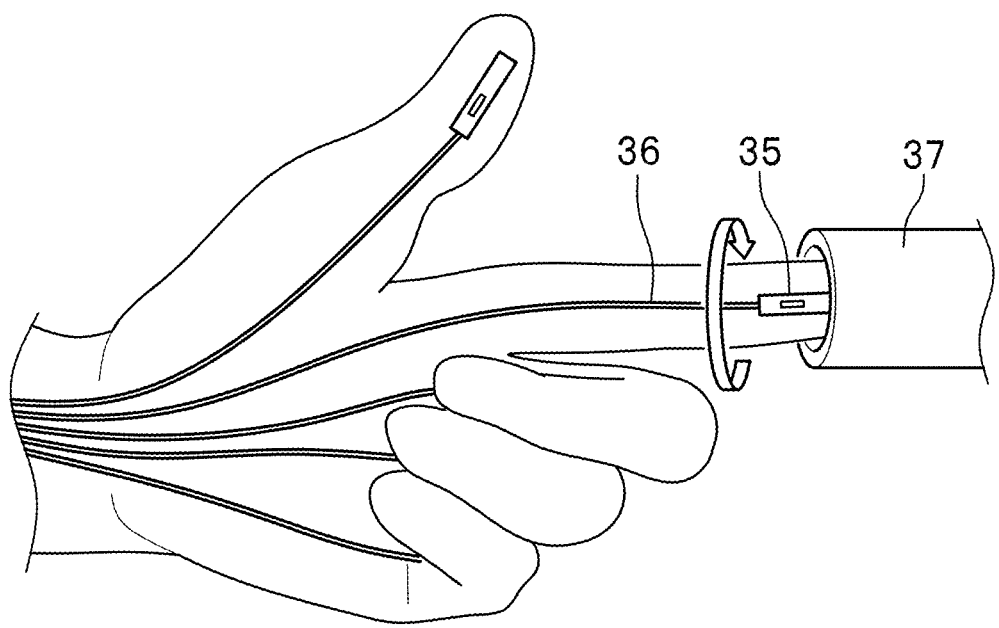
FIG. 26A illustrates a case of checking an object (pipe) for breakage with flexible imaging by the flexible array sensor in FIG. 25.
Figure 26B:
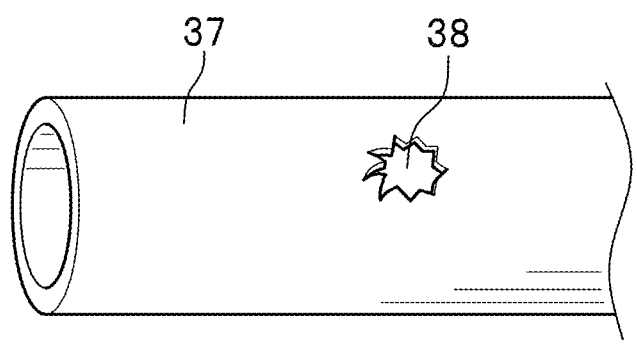
FIG. 26B is an enlarged view of the checked object (pipe) in FIG. 26A to show a breakage.
Figure 27:
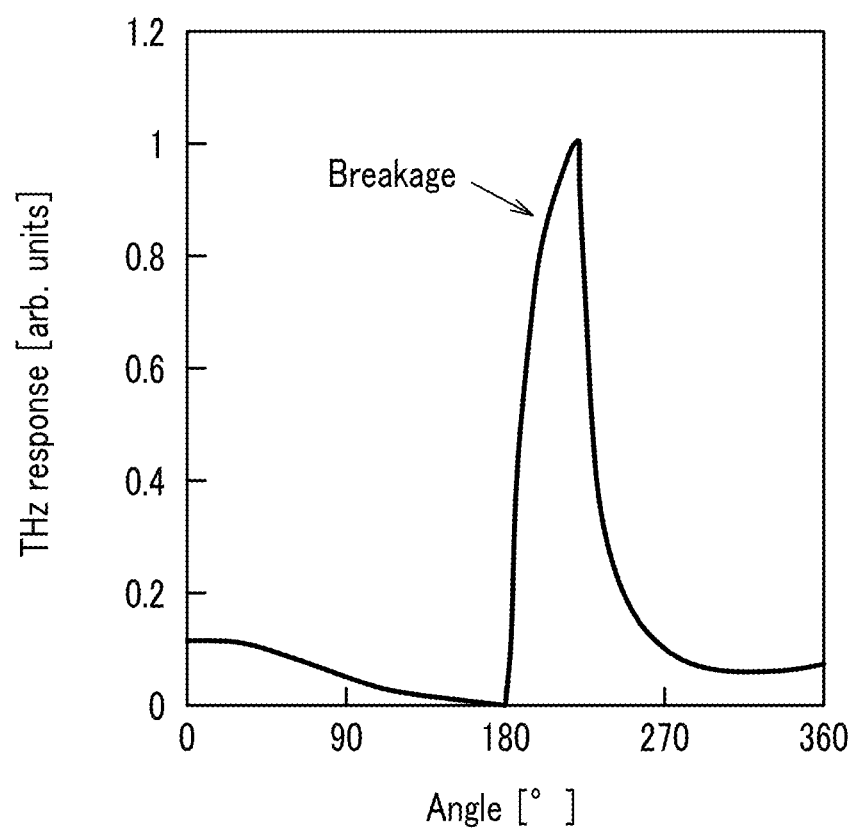
FIG. 27 is a chart showing a checking result when the flexible array sensor 35 is turned all around inside the checked object (pipe) in FIG. 26A so as to be checked for breakage.

FIGS. 26A and 26B illustrate a case of checking an object (pipe) for breakage in flexible imaging by the flexible array sensor 35 in FIG. 25, where FIG. 26A illustrates scanning the object and FIG. 26B is an enlarged view of a checked object (pipe) 37 in FIG. 26A to show a breakage 38. FIG. 27 is a chart showing a checking result when the flexible array sensor 35 is turned all around inside the object (pipe) in FIG. 26A so as to be checked for breakage.

As shown in FIG. 26A, a fingertip having the flexible array sensor 35 attached thereto is inserted into the checked object (pipe) 37, and then turned as indicated by an arrow in FIG. 26A. The flexible array sensor 35 attached to the fingertip is freely turned in the checked object (pipe) 37 to achieve multi-view scanning once the flexible array sensors 35 is turned all therearound for scanning. The breakage 38 in the checked object (pipe) 37 is clearly detected, as shown in FIG. 27. The above-described case is an example of checking by the flexible array sensor 35 attached to one fingertip, but a THz scanner for an object never been checked may be implemented to use checking results by the flexible array sensors 35 attached to five fingertips. For example, a three-dimensional object such as a spherical object may be held with a hand having the flexible array sensors 35 attached to fingertips or rubbed with the fingertips to execute omnidirectional inspection of the three-dimensional object.

As described above, the flexible array sensor 35 can be attached to any object such as a fingertip, to remove existing restrictions on imaging conditions such as the shape and position of a checked object. As a result, the application range of the flexible array sensor 35 (terahertz wave detection device) can be greatly expanded.

As described above, the flexible array sensor 30 according to the present embodiment includes: the terahertz wave detection element 10 inclusive of the flexible single-walled carbon nanotube film 11, and the first and second electrodes 12, 13 disposed to face each other on the two-dimensional plane of the single-walled carbon nanotube film 11; and the flexible substrate 20 having flexibility to support the terahertz wave detection element 10 so as to be freely curved. The flexible substrate 20 is formed in a curved or cylindrical shape, and the terahertz wave detection element 10 is preferably arrayed on the flexible substrate 20 formed in a curved or cylindrical shape.

As described above, a two-dimensional image is obtained merely with the flexible array sensor 30 being moved in one direction, to allow for observation at high speed with high sensitivity and high accuracy. That is, many of the existing techniques belong to a scanning type and therefore it takes time for imaging. In contrast, as the plurality of terahertz wave detection elements 10 are arrayed on the flexible substrate 20 in the present embodiment, a two-dimensional image is obtained merely with the flexible array sensor 30 being moved in the direction orthogonal to the array direction, to execute checking at high speed with high sensitivity and high accuracy. Besides, temporal changes can be tracked.

In particular, as the flexible array sensor 30 is a camera that can be bent, full-field checking is made instantaneously. The flexible array sensor 30 allows for implementing omni-directional inspection with no large checking system. This is a significant advantage over existing THz detectors. In addition, the flexible array sensor 30 may be applicable to sensing or medical applications, such as to use as a living body sensor utilizing a flexible property and to affix to a human body. Further, the flexible array sensor 30 may be applicable to a wearable and high-speed wave-signal processing device. Furthermore, the flexible array sensor 30 may be applicable to various applications to take advantage of the flexible property, such as a matrix tactile sensor for health management and monitoring, and combination with a thin film heater or a temperature/infrared sensor.

In the present embodiment, types and thicknesses of the electrodes were changed to see whether detection sensitivity was improved. Imaging by multi-element array sensor makes material, which is invisible with visible light, visible. In addition, a single camera is capable of imaging waves ranging from sub-terahertz waves to infrared. Although such imaging is currently feasible at 1 to 30 THz, it should be feasible at sub-terahertz to several hundred THz in principle.

The present invention is not limited to the embodiment described above and includes other modifications and applications without departing from the scope of the present invention as claimed in appended claims. For example, in the present embodiment, the single-walled carbon nanotube film 11 is used, but the carbon nanotube film does not have to be a single-walled film as long as a carbon nanotube film having flexibility is used. That is, the carbon nanotube film may be a flexible multi-walled carbon nanotube film.

In addition, the foregoing embodiment has been described in detail for the purpose of illustration of the present invention and is not necessarily limited to the configuration having all the components as described above. The configuration of one embodiment may partly be replaced with that of another embodiment, or the configuration of one embodiment may be added with that of another embodiment.

The configurations of the embodiments may partly be added or replaced with other configurations, or may be deleted. Further, although the name of the terahertz wave detection device is used in the above-described embodiment, this is for convenience sake, and the name may be a terahertz wave detector or the like.

The invention claimed is:

1. A terahertz wave detection device comprising:
one or more terahertz wave detection elements, each configured to include:
a carbon nanotube film having flexibility; and
a first electrode and a second electrode that are disposed to face each other on a two-dimensional plane of the carbon nanotube film,
wherein the carbon nanotube film is a carbon nanotube having a ratio of the value of a standard deviation multiplied by 3 divided by a mean diameter and being greater than 0.20 but less than 0.60.

2. The terahertz wave detection device as claimed in claim 1, further comprising:
a flexible substrate having flexibility that supports the one or more terahertz wave detection elements so as to be freely curved.

3. The terahertz wave detection device as claimed in claim 1,
wherein the one or more terahertz wave detection elements are arrayed on the flexible substrate.

4. The terahertz wave detection device as claimed in claim 1, further comprising:
a flexible substrate formed in a curved or cylindrical shape,
wherein the one or more terahertz wave detection elements are arrayed on the flexible substrate formed in a curved or cylindrical shape.

5. The terahertz wave detection device as claimed in claim 1, further comprising:
a flexible substrate formed in a cup shape as being convex upward,
wherein the one or more terahertz wave detection elements are arrayed concentrically about a vertex of the flexible substrate in a cup shape.

6. The terahertz wave detection device as claimed in claim 1, further comprising:
one or more terahertz oscillators that transmit terahertz waves to be received by the one or more terahertz wave detection elements.

7. The terahertz wave detection device as claimed in claim 1, wherein
the carbon nanotube film contains 50% by weight or more of the single-walled carbon nanotubes.

8. A terahertz wave detection device comprising:
one or more terahertz wave detection element, each configured to include:
a carbon nanotube film having flexibility;
a first electrode and a second electrode that are disposed to face each other on a two-dimensional plane of the carbon nanotube film; and
one or more terahertz oscillators that transmit terahertz waves to be received by the one or more terahertz wave detection elements,
wherein the one or more terahertz wave detection elements receive terahertz waves diffusely reflected by a checked object, and
wherein the carbon nanotube film is a carbon nanotube having a ratio of the value of a standard deviation multiplied by 3 divided by a mean diameter and being greater than 0.20 but less than 0.60.

9. A terahertz wave detection device comprising:
one or more terahertz wave detection elements, each configured to include:
a carbon nanotube film having flexibility;
a first electrode and a second electrode that are disposed to face each other on a two-dimensional plane of the carbon nanotube film; and
one or more terahertz oscillators that transmit terahertz waves to be received by the one or more terahertz wave detection elements,
wherein the one or more terahertz oscillators are arranged on the carbon nanotube film along with the one or more terahertz wave detection elements, and
wherein the carbon nanotube film is a carbon nanotube having a ratio of the value of a standard deviation multiplied by 3 divided by a mean diameter and being greater than 0.20 but less than 0.60.

10. A terahertz wave detection system comprising:
a terahertz wave detection device as claimed in claim 1; and
a data collection device to collect physical data detected by the terahertz wave detection device.

11. A terahertz wave detection system comprising:
a terahertz wave detection device as claimed in claim 2; and
a data collection device to collect physical data detected by the terahertz wave detection device.

12. A terahertz wave detection system comprising:
a terahertz wave detection device as claimed in claim 3; and
a data collection device to collect physical data detected by the terahertz wave detection device.

13. A terahertz wave detection system comprising:
a terahertz wave detection device as claimed in claim 4; and
a data collection device to collect physical data detected by the terahertz wave detection device.

14. A terahertz wave detection system comprising:
a terahertz wave detection device as claimed in claim 5; and
a data collection device to collect physical data detected by the terahertz wave detection device.

15. A terahertz wave detection system comprising:
a terahertz wave detection device as claimed in claim 6; and
a data collection device to collect physical data detected by the terahertz wave detection device.

16. A terahertz wave detection system comprising:
a terahertz wave detection device as claimed in claim 7; and
a data collection device to collect physical data detected by the terahertz wave detection device.

17. A terahertz wave detection system comprising:
a terahertz wave detection device as claimed in claim 8; and
a data collection device to collect physical data detected by the terahertz wave detection device.

18. A terahertz wave detection system comprising:
a terahertz wave detection device as claimed in claim 9; and
a data collection device to collect physical data detected by the terahertz wave detection device.

* * * * *